United States Patent
Zuluaga

(10) Patent No.: US 7,450,241 B2
(45) Date of Patent: Nov. 11, 2008

(54) DETECTING VULNERABLE PLAQUE

(75) Inventor: Andres F. Zuluaga, Boston, MA (US)

(73) Assignee: InfraReDx, Inc., Burlington, MA (US)

( * ) Notice: Subject to any disclaimer, the term of this patent is extended or adjusted under 35 U.S.C. 154(b) by 263 days.

(21) Appl. No.: 11/241,726

(22) Filed: Sep. 30, 2005

(65) Prior Publication Data

US 2007/0076212 A1   Apr. 5, 2007

(51) Int. Cl.
 *G01J 3/45* (2006.01)
 *G01B 9/02* (2006.01)
(52) U.S. Cl. .................. 356/479; 356/451; 356/477
(58) Field of Classification Search .......... 356/477, 356/479, 450–451, 481; 600/114, 407, 505, 600/437
 See application file for complete search history.

(56) References Cited

U.S. PATENT DOCUMENTS

| | | | |
|---|---|---|---|
| 4,375,818 A | | 3/1983 | Suwaki et al. |
| 4,504,727 A | | 3/1985 | Melcher et al. |
| 4,794,931 A | | 1/1989 | Yock |
| 4,873,989 A | * | 10/1989 | Einzig .................. 600/505 |
| 5,029,588 A | | 7/1991 | Yock et al. |
| 5,167,233 A | | 12/1992 | Eberle et al. |
| 5,377,008 A | * | 12/1994 | Ridgway et al. ......... 356/481 |
| 5,398,670 A | * | 3/1995 | Ortiz et al. ............. 600/114 |
| 5,576,013 A | | 11/1996 | Williams et al. |
| 5,681,277 A | | 10/1997 | Edwards et al. |
| 5,716,595 A | | 2/1998 | Goldenberg |
| 5,725,494 A | | 3/1998 | Brisken |
| 5,728,092 A | | 3/1998 | Doiron et al. |
| 5,916,210 A | | 6/1999 | Winston |
| 5,924,997 A | | 7/1999 | Campbell |
| 5,935,075 A | | 8/1999 | Casscells et al. |
| 5,964,727 A | | 10/1999 | Edwards et al. |
| 6,016,440 A | | 1/2000 | Simon et al. |
| 6,022,309 A | | 2/2000 | Celliers et al. |

(Continued)

FOREIGN PATENT DOCUMENTS

WO    WO 90/1325/3    11/1990

(Continued)

OTHER PUBLICATIONS de Korte et al., "Identification of Atherosclerotic Plaque Components With Intravascular Ultrasound Elastography In Vivo: A Yucatan Pig Study", Circulation, 105:1627-1630, (Apr. 9, 2002).

(Continued)

*Primary Examiner*—Sang Nguyen
(74) *Attorney, Agent, or Firm*—Fish & Richardson P.C.

(57) ABSTRACT

An apparatus and associated method for detecting vulnerable plaque within a lumen defined by an intraluminal wall is described. The apparatus includes a probe having a distal portion and a proximal portion. The apparatus includes an optical waveguide extending along the probe. The optical waveguide is configured to carry optical radiation between the distal and proximal portions, and has a distal end in communication with the intraluminal wall. The apparatus includes an interferometer coupled to the optical waveguide and configured to provide an interference signal for subsurface imaging of the intraluminal wall, and a processing module configured to provide spectroscopic information from detected intensity of light collected from the intraluminal wall.

17 Claims, 20 Drawing Sheets

U.S. PATENT DOCUMENTS

| | | | |
|---|---|---|---|
| 6,035,229 A * | 3/2000 | Silverstein et al. | 600/473 |
| 6,054,449 A | 4/2000 | Robinson et al. | |
| 6,134,003 A | 10/2000 | Tearney et al. | |
| 6,191,862 B1 * | 2/2001 | Swanson et al. | 356/479 |
| 6,210,393 B1 | 4/2001 | Brisken | |
| 6,296,619 B1 | 10/2001 | Brisken et al. | |
| 6,421,164 B2 * | 7/2002 | Tearney et al. | 359/287 |
| 6,485,413 B1 | 11/2002 | Boppart et al. | |
| 6,507,747 B1 * | 1/2003 | Gowda et al. | 600/407 |
| 6,615,071 B1 | 9/2003 | Casscells et al. | |
| 6,654,630 B2 | 11/2003 | Zuluaga et al. | |
| 6,690,958 B1 | 2/2004 | Walker et al. | |
| 6,692,430 B2 | 2/2004 | Adler | |
| 6,701,181 B2 | 3/2004 | Tang et al. | |
| 6,949,072 B2 | 9/2005 | Furnish et al. | |
| 7,190,464 B2 * | 3/2007 | Alphonse | 356/479 |
| 7,376,456 B2 * | 5/2008 | Marshik-Geurts et al. | 600/473 |
| 2003/0028114 A1 | 2/2003 | Casscells, III et al. | |
| 2003/0199767 A1 | 10/2003 | Cespedes et al. | |
| 2003/0236443 A1 | 12/2003 | Cespedes et al. | |
| 2004/0034290 A1 | 2/2004 | Zuluaga | |
| 2004/0260182 A1 | 12/2004 | Zuluaga et al. | |
| 2005/0018202 A1 | 1/2005 | Wang | |
| 2005/0107706 A1 | 5/2005 | Zuluaga et al. | |
| 2005/0190372 A1 | 9/2005 | Dogariu | |
| 2006/0039004 A1 | 2/2006 | De Boer et al. | |

FOREIGN PATENT DOCUMENTS

| | | |
|---|---|---|
| WO | WO/1999/057507 | 11/1999 |
| WO | WO 00/32102 A1 | 6/2000 |
| WO | WO 02/04929 A2 | 1/2002 |
| WO | WO 2005/047813 A | 5/2005 |
| WO | WO 2005/059510 A2 | 6/2005 |

OTHER PUBLICATIONS

Yun et al., "Removing the Depth-Degeneracy in Optical Frequency Domain Imaging With Frequency Shifting", Optics Express, vol. 12, No. 20 pp. 4822-4828, Oct. 4, 2004.

Yun et al., "High-Speed Optical Frequency-Domain Imaging", Optics Express, vol. 11, No. 22 pp. 2953-2963, Oct. 27, 2003.

Fercher et al., "Measurement of Intraocular Distances by Backscattering Spectral Interferometry", Optics Communications, vol. 117, pp. 43-48, May 15, 1995.

* cited by examiner

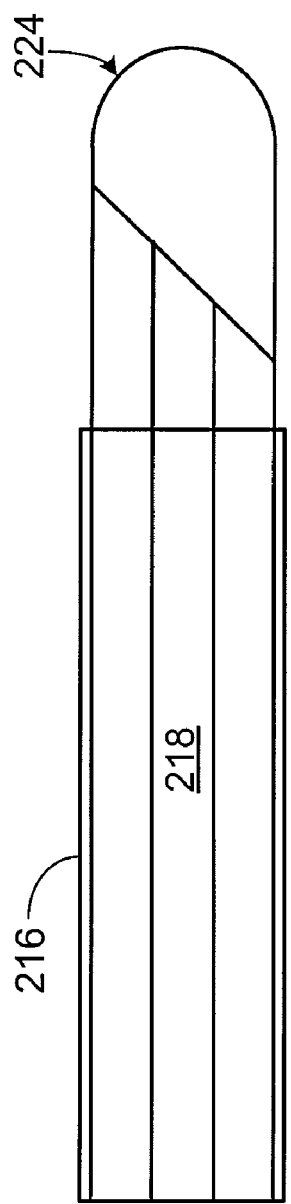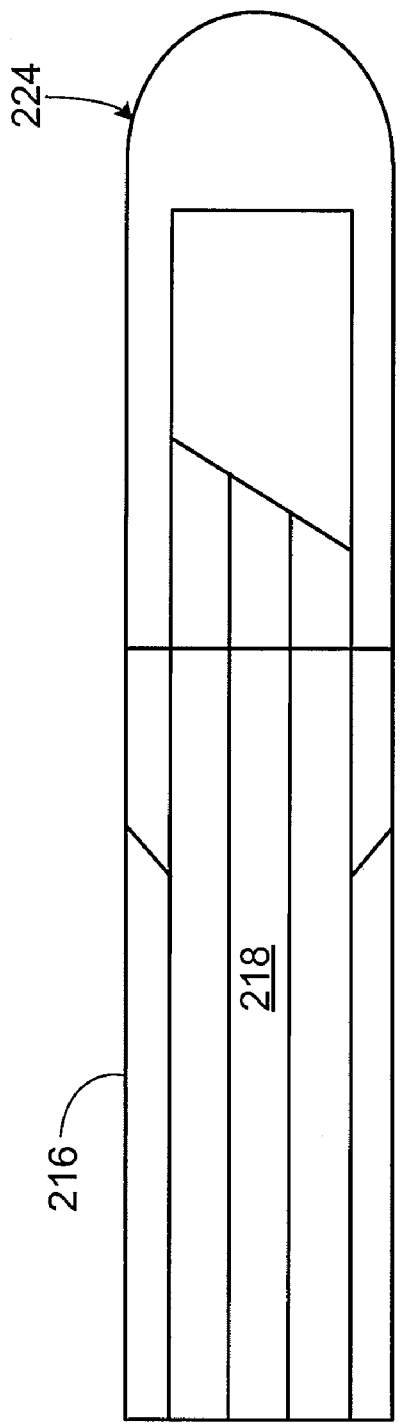
FIG. 4F
FIG. 4G

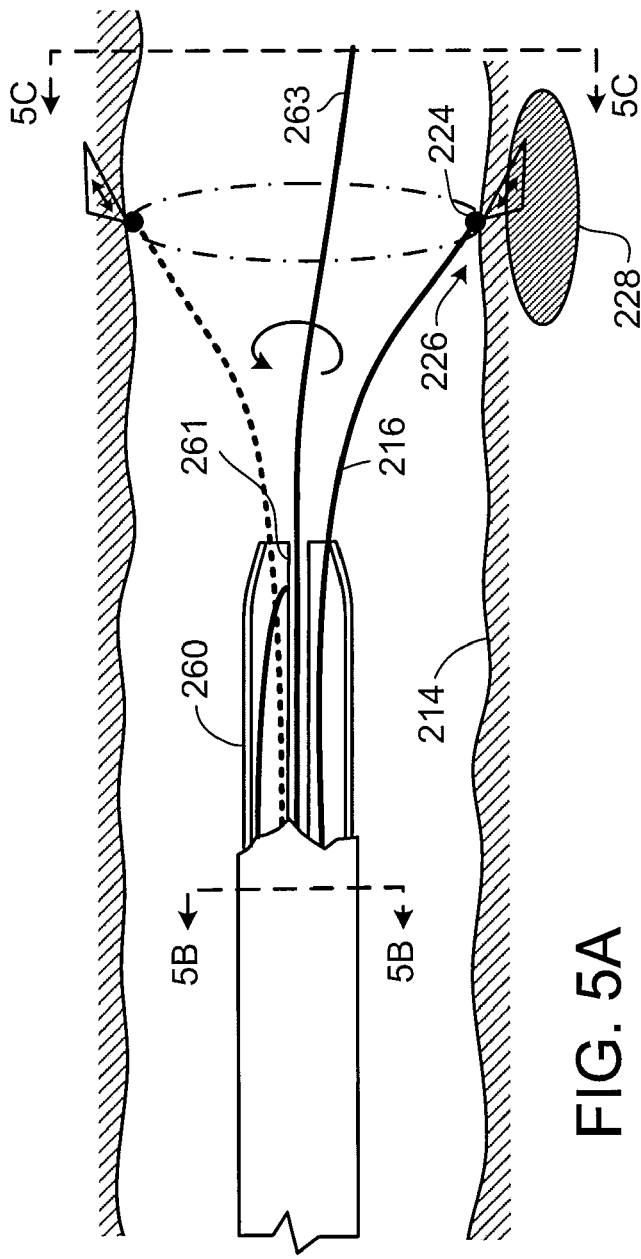
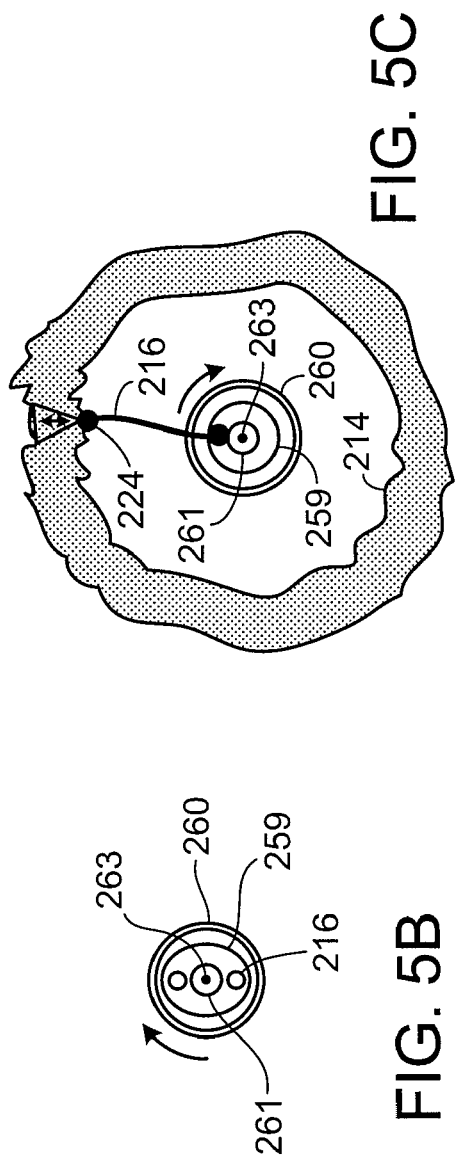
FIG. 5A
FIG. 5B
FIG. 5C

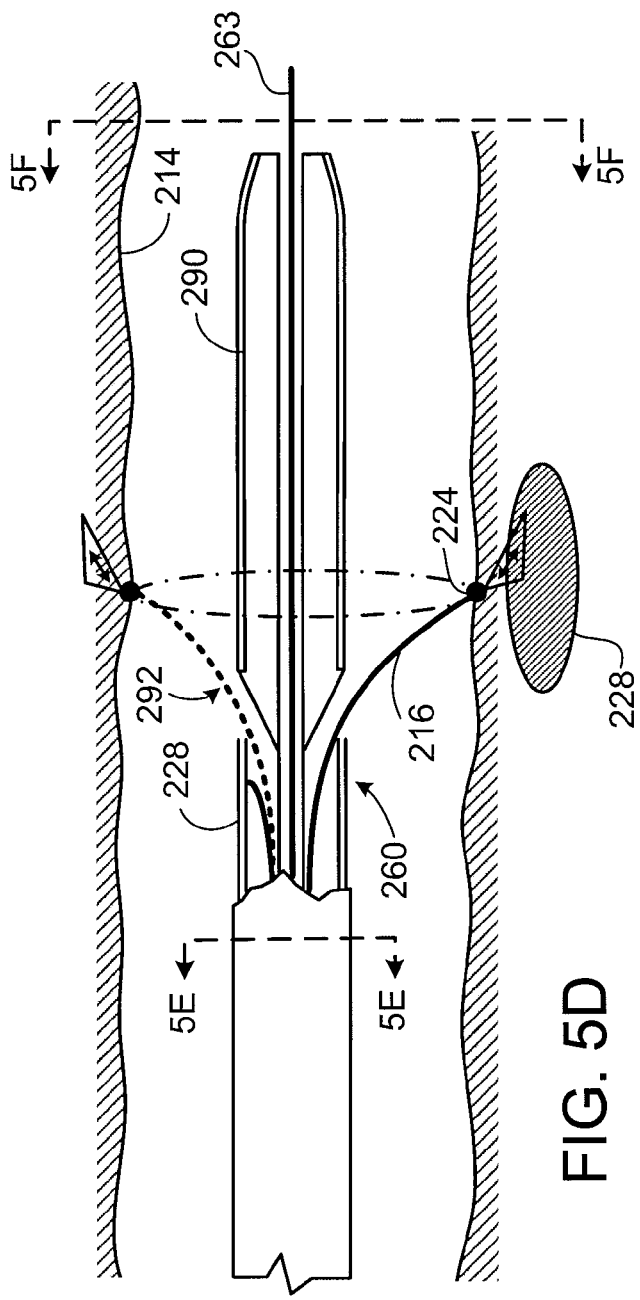
FIG. 5D
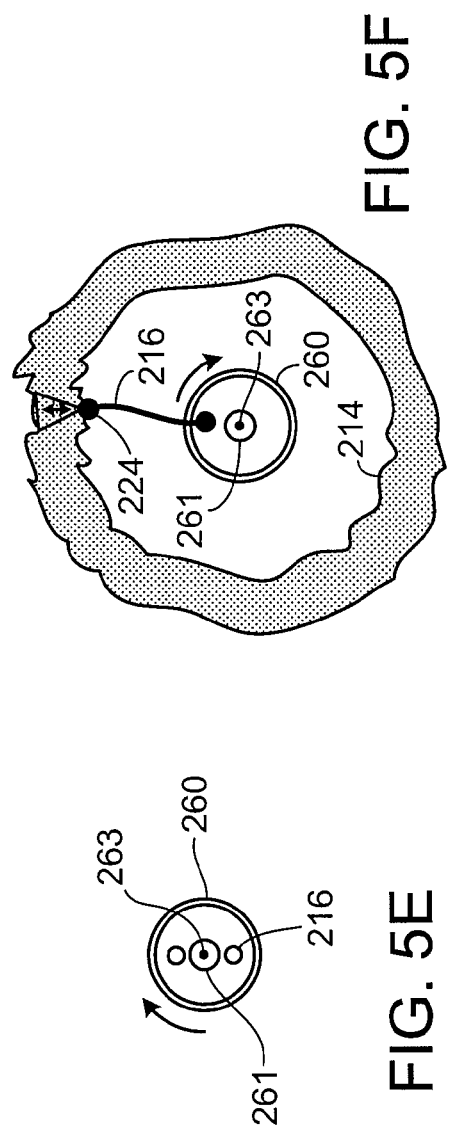
FIG. 5F
FIG. 5E

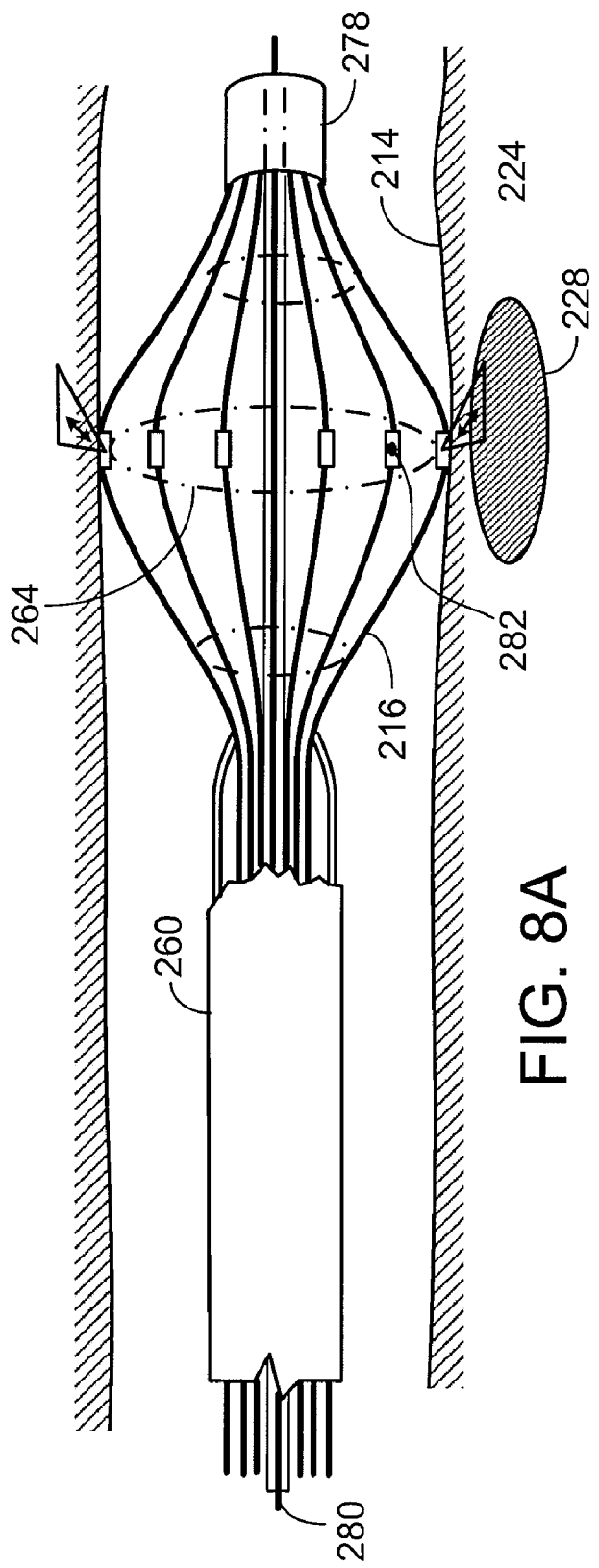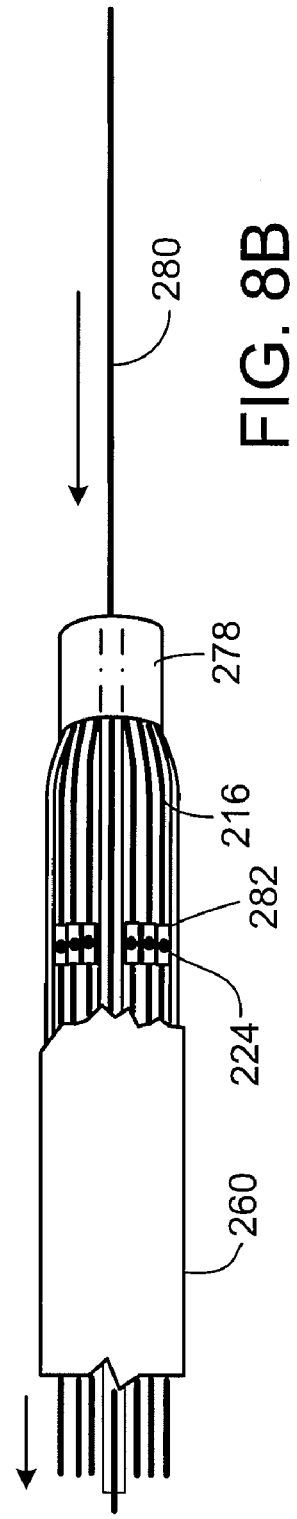

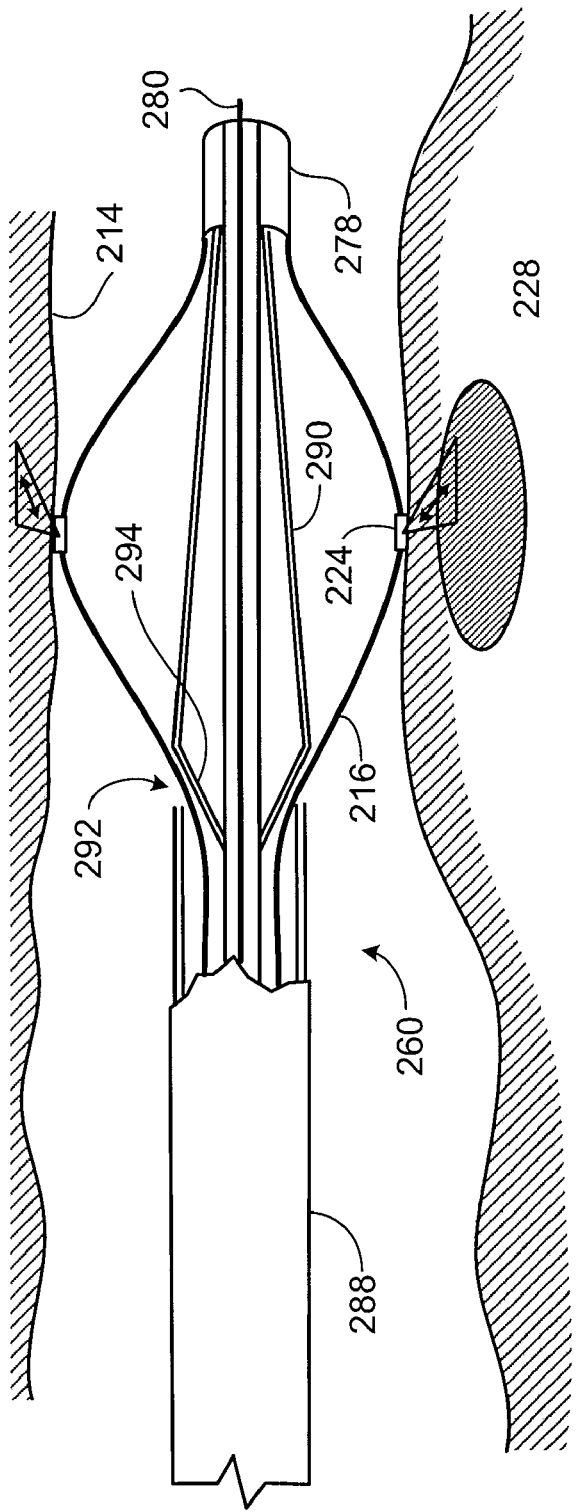
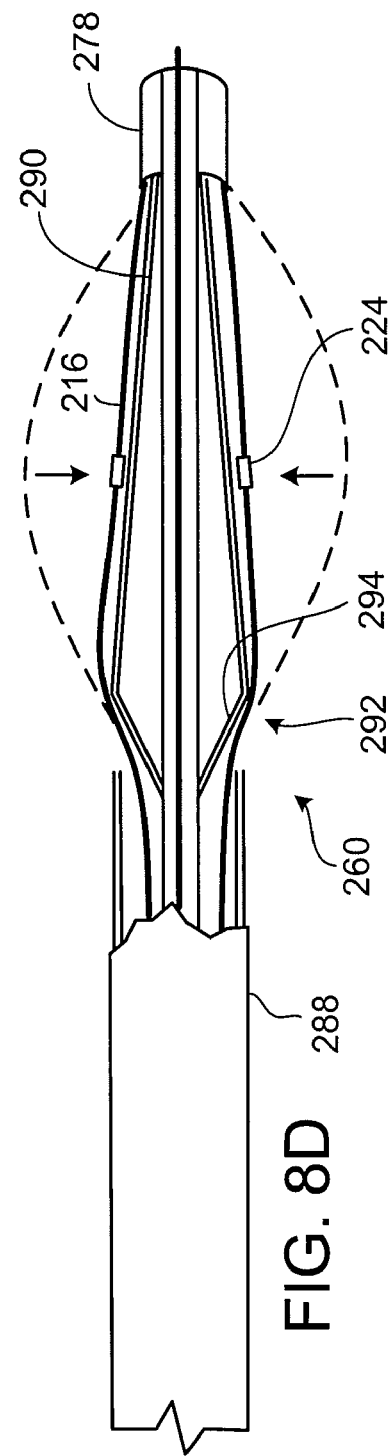
FIG. 8C
FIG. 8D

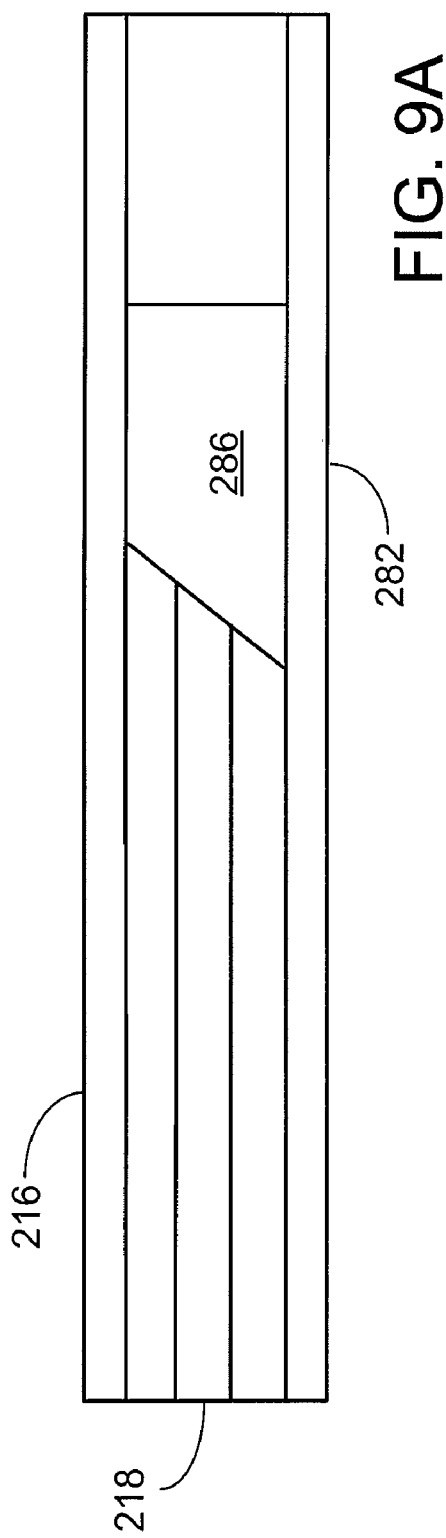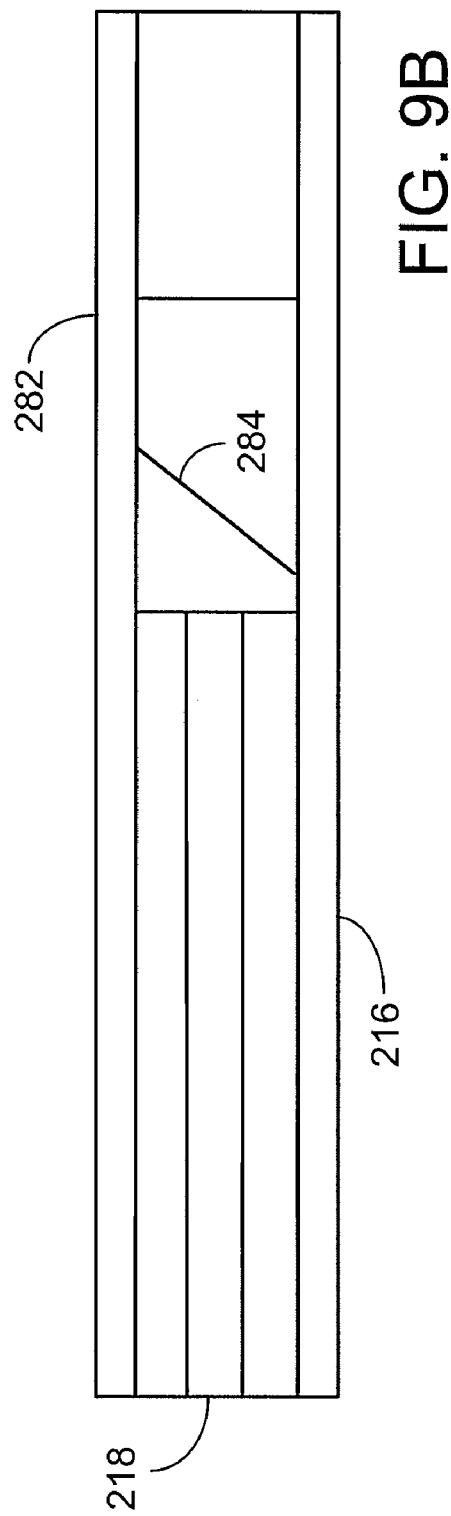

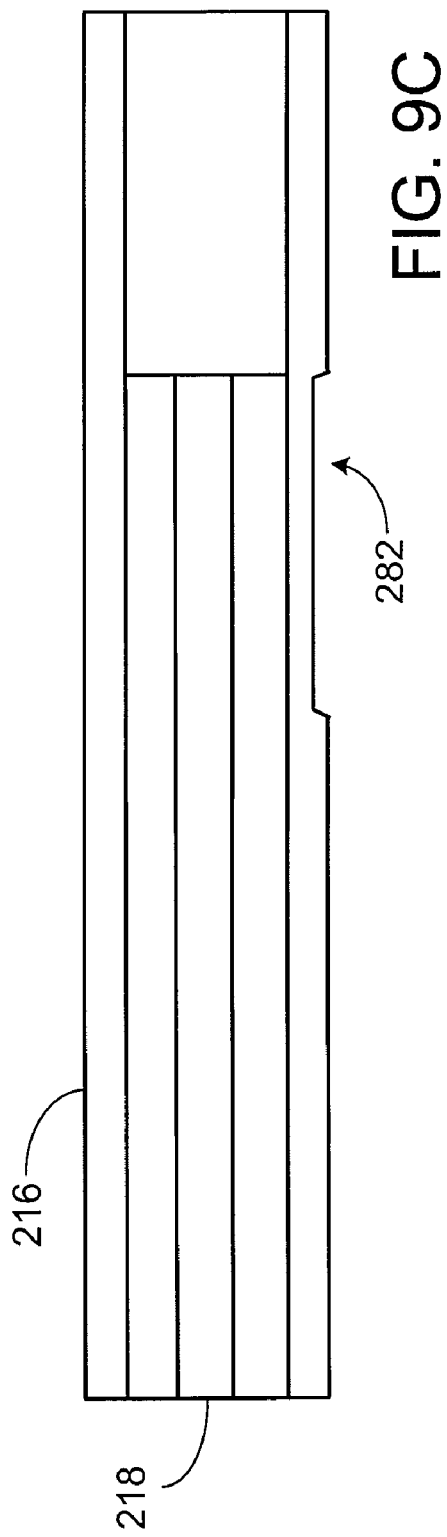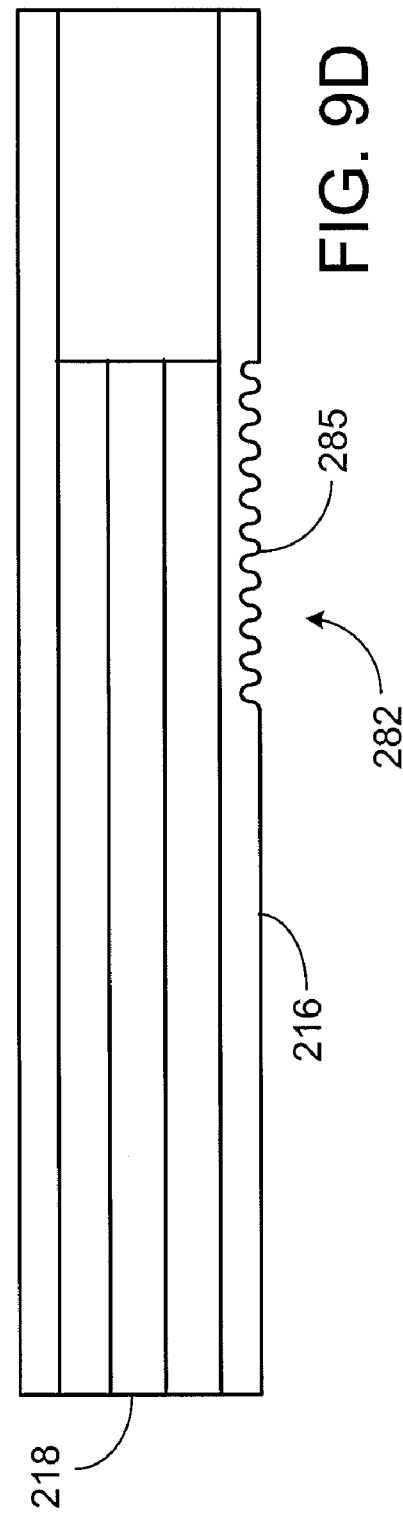

DETECTING VULNERABLE PLAQUE

FIELD OF INVENTION

The invention relates to devices for luminal diagnostics, and in particular, to detecting vulnerable plaque.

BACKGROUND

Atherosclerosis is a vascular disease characterized by a modification of the walls of blood-carrying vessels. Such modifications, when they occur at discrete locations or pockets of diseased vessels, are referred to as plaques. Certain types of plaques are associated with acute events such as stroke or myocardial infarction. These plaques are referred to as "vulnerable plaques." A vulnerable plaque typically includes a lipid-containing pool separated from the blood by a thin fibrous cap. In response to elevated intraluminal pressure or vasospasm, the fibrous cap can become disrupted, exposing the contents of the plaque to the flowing blood. The resulting thrombus can lead to ischemia or to the shedding of emboli.

One method of locating vulnerable plaque is to peer through the arterial wall with infrared light. To do so, one inserts a catheter through the lumen of the artery. The catheter includes a delivery fiber for illuminating a spot on the arterial wall with infrared light. A portion of the light penetrates the blood and arterial wall, scatters off structures within the wall and re-enters the lumen. This re-entrant light can be collected by a collection fiber within the catheter and subjected to spectroscopic analysis. This type of diffuse reflectance spectroscopy can be used to determine chemical composition of arterial tissue, including key constituents believed to be associated with vulnerable plaque such as lipid content.

Another method of locating vulnerable plaque is to use optical coherence tomography (OCT) to image the arterial tissue surrounding the lumen. To use this method, one also inserts a catheter through the lumen of the artery. The catheter includes a fiber that transports light having a limited coherence length through imaging optics to the arterial wall. The backscattered light couples back into the fiber towards an interferometer. The interferometer provides a cross-correlation signal that is used to map the shape of the arterial tissue. This map of the morphology of the arterial wall can be used to detect the fibrous cap and other structural characteristics associated with vulnerable plaque.

SUMMARY

The invention is based on the recognition that combining two detection modalities, infrared spectroscopy and sub-surface imaging (e.g., OCT), in the same probe increases the probe's ability to detect lesions such as vulnerable plaque.

In one aspect, the invention features an apparatus for detecting vulnerable plaque within a lumen defined by an intraluminal wall. The apparatus includes a probe having a distal portion and a proximal portion. The apparatus includes an optical waveguide extending along the probe. The optical waveguide is configured to carry optical radiation between the distal and proximal portions, and has a distal end in communication with the intraluminal wall. The apparatus includes an interferometer coupled to the optical waveguide and configured to provide an interference signal for sub-surface imaging of the intraluminal wall, and a processing module configured to provide spectroscopic information from detected intensity of light collected from the intraluminal wall.

This aspect can include one or more of the following features.

The processing module is configured to receive the detected intensity of light collected from the intraluminal wall by the optical waveguide.

The apparatus further includes a second optical waveguide extending along the probe, the second optical waveguide being configured to carry optical radiation between the distal and proximal portions, and having a distal end in communication with the intraluminal wall.

The processing module is configured to receive the detected intensity of light collected from the intraluminal wall by the second optical waveguide.

The interferometer is configured to provide an interference signal for sub-surface imaging by performing optical coherence tomography.

The interferometer is configured to provide an interference signal for sub-surface imaging by performing optical frequency domain reflectometry.

In another aspect, the invention features an apparatus for detecting vulnerable plaque within a lumen defined by an intraluminal wall. The apparatus includes a probe having a distal portion and a proximal portion. The apparatus includes a first optical waveguide extending along the probe, the first optical waveguide being configured to carry optical radiation between the distal and proximal portions, and having a distal end in communication with the intraluminal wall. The apparatus includes a second optical waveguide extending along the probe, the second optical waveguide being configured to carry optical radiation between the distal and proximal portions, and having a distal end in communication with the intraluminal wall. The apparatus includes a third optical waveguide coupled to a portion of the second optical waveguide.

This aspect can include one or more of the following features.

The apparatus further includes an optical coupler in optical communication with the distal end of the first optical waveguide, the optical coupler being configured to transmit optical radiation between the first optical waveguide and the intraluminal wall.

The apparatus further includes an optical coupler in optical communication with the distal end of the second optical waveguide, the optical coupler being configured to transmit optical radiation between the second optical waveguide and the intraluminal wall.

The apparatus further includes a fourth optical waveguide coupled to a portion of the first optical waveguide.

The apparatus further includes a variable-delay coupler configured to couple optical radiation from the third optical waveguide into the fourth optical waveguide with a variable optical group delay.

The variable-delay coupler is configured to scan the variable optical group delay by an amount corresponding to a coherence length of a source of optical radiation.

The apparatus further includes an optical source configured to couple optical radiation into the second and third optical waveguides.

The apparatus further includes an optical detector configured to receive optical radiation from the first and fourth optical waveguides.

The apparatus further includes a variable-delay reflector configured to reverse the direction of propagation of optical radiation in the third optical waveguide with a variable optical group delay.

The variable-delay reflector is configured to scan the variable optical group delay by an amount corresponding to a coherence length of a source of optical radiation.

The apparatus further includes an optical source configured to couple optical radiation into the second and third optical waveguides; and a first optical detector configured to receive optical radiation from the second and third optical waveguides.

The apparatus further includes a second optical detector configured to receive optical radiation from the first optical waveguide.

The optical coupler can be an atraumatic light-coupler configured to atraumatically contact the intraluminal wall.

In another aspect, the invention features a method for detecting vulnerable plaque within a lumen defined by an intraluminal wall. The method includes inserting a distal portion of a probe into the lumen. The method includes providing optical radiation to the intraluminal wall through an optical waveguide extending along the probe. The method includes combining reference optical radiation with optical radiation scattered from the intraluminal wall, and returning through the optical waveguide, to provide an interference signal for sub-surface imaging of the intraluminal wall. The method includes processing a detected intensity of light collected from the intraluminal wall to extract spectroscopic information.

As used herein, "infrared" means infrared, near infrared, intermediate infrared, far infrared, or extreme infrared.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE FIGURES

FIGS. 4A-G are exemplary atraumatic light-couplers for an optical fiber.

FIGS. 5A-F are schematic views of single-probe spectroscopes.

FIGS. 8A-8F are schematic views of multi-probe spectroscopes in which the atraumatic light-couplers are along the sides of the probes.

FIGS. 9A-D are views of exemplary atraumatic light-couplers for the probes in FIGS. 8A-H.

DETAILED DESCRIPTION

The vulnerability of a plaque to rupture can be assessed by detecting a combination of attributes such as macrophage presence, local temperature rise, and a lipid-rich pool covered by a thin fibrous cap. Some detection modalities are only suited to detecting one of these attributes.

FIGS. 1A-1D show embodiments 100A-100D of a vulnerable plaque detection system (VPDS) that combines two detection modalities for identifying vulnerable plaque 102 in an arterial wall 104 of a patient. The combination of both chemical analysis, using infrared spectroscopy to detect lipid content, and morphometric analysis, using sub-surface imaging (e.g., optical coherence tomography (OCT) or optical frequency domain reflectometry (OFDR)) to detect cap thickness, enables greater selectivity in identifying potentially vulnerable plaques than either detection modality alone.

Figure 1A:
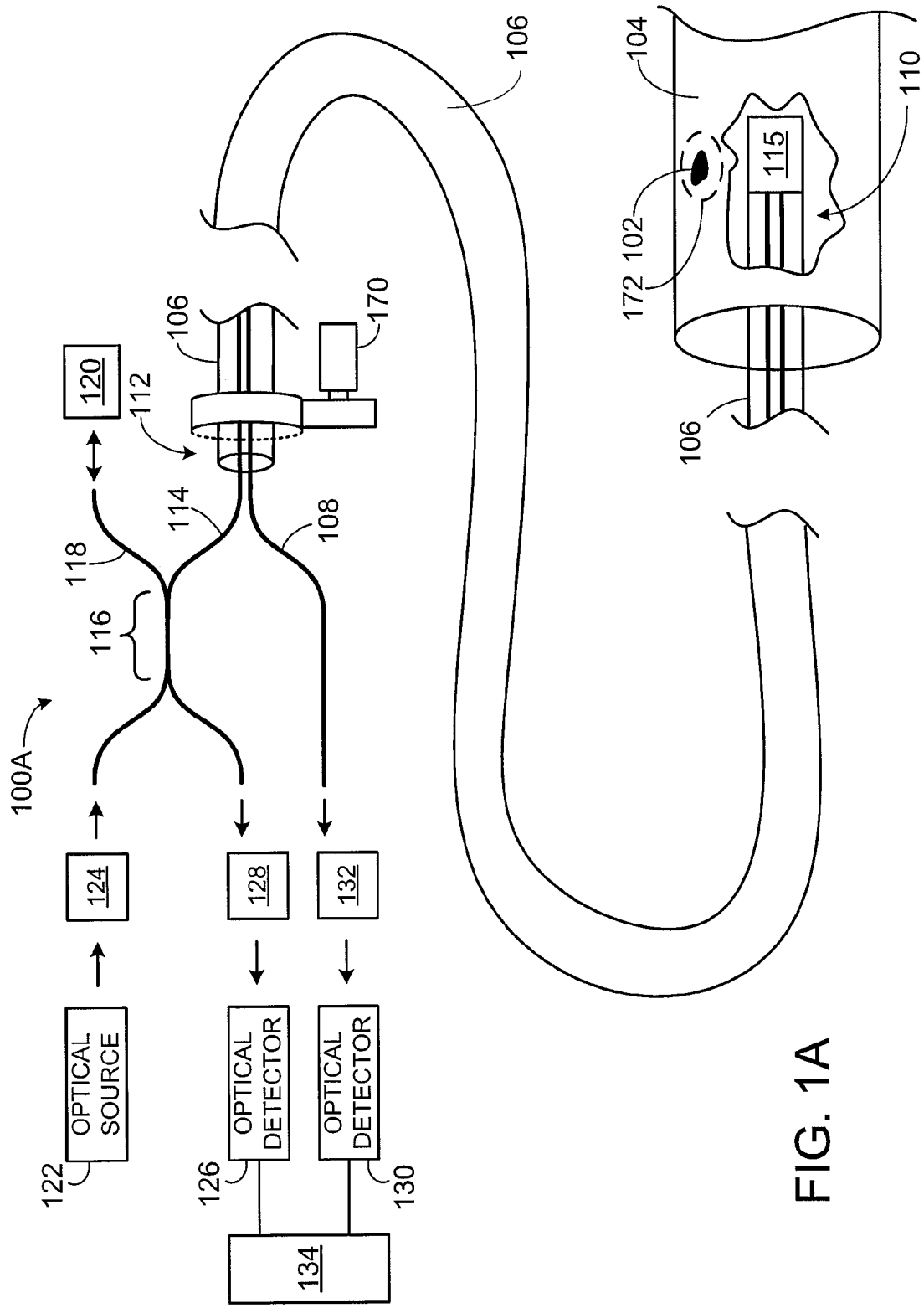
FIGS. 1A-1D are schematic diagrams of embodiments of a vulnerable plaque detection system for identifying vulnerable plaque.

Referring to FIG. 1A, in a first embodiment, a VPDS 100A includes a probe 106 to be inserted into a selected artery, e.g. a coronary artery, of the patient. A first optical waveguide 108 (e.g., an optical fiber) extends between a distal end 110 and a proximal end 112 of the probe 106 for collecting scattered optical radiation for spectroscopic analysis of the arterial wall 104. A second optical waveguide 114 also extends between the distal end 110 and the proximal end 112 of the probe 106 and is part of an interferometer for sub-surface imaging of the arterial wall 104. Optical radiation for both sub-surface imaging and spectroscopic analysis is delivered to the arterial wall through the second optical waveguide 114. An optical delivery and collection head 115 includes one or more optical couplers in optical communication with distal ends of the first and second optical waveguides to couple light from the arterial wall into the first and second optical waveguides, as described in more detail below.

The interferometer for sub-surface imaging includes a beamsplitter 116 that mixes the optical radiation from the second optical waveguide 114 with optical radiation from a third optical waveguide 118. In this embodiment, the beamsplitter 116 is a 50/50 fused-fiber 2×2 coupler with a 50% power splitting ratio, two input ports and two output ports. Alternatively, any of a variety of optical beam splitting and recombining devices and techniques may be used. The second optical waveguide 114 includes an optical fiber with one end that extends into the probe 106 and another end that is coupled (e.g., fusion spliced or butt-coupled) to an optical fiber output port of the beamsplitter 116. The third optical waveguide 118 includes an optical fiber with one end that is coupled to the other optical fiber output port of the beamsplitter 116 and another end that is coupled to a variable-delay reflector 120 (e.g., a translatable mirror, a tiltable grating, a tunable fiber loop, etc.) to reverse the direction of propagation of optical radiation in the third optical waveguide with a variable optical group delay. Alternatively, either or both of the second and/or third optical waveguides can have optical fibers that are integral with the beamsplitter 116.

An optical source 122 provides infrared light that is coupled into the second and third optical waveguides via an optical coupler 124 that is in optical communication with a first optical fiber input port of the beamsplitter 116. A first optical detector 126 is in optical communication with a second optical fiber input port of the beamsplitter 116, via an optical coupler 128, to receive optical radiation from the second and third optical waveguides (114 and 118). The optical radiation fields from the second and third optical waveguides sum to produce an interference pattern of optical intensity at the first optical detector 126. A second optical detector 130 is in optical communication with the first optical waveguide 108, via an optical coupler 132.

The first and second optical detectors each provide an electrical signal indicative of optical intensity to a processing module 134. The processing module 134 converts this signal into digital data (e.g., using an analog-to-digital ("A/D") converter) that can be analyzed by a digital processor.

The intensity signal produced by the first optical detector 126 is used for sub-surface imaging. The processing module 134 extracts from this signal sub-surface imaging information about the arterial wall 104.

The intensity signal produced by the second optical detector 130 is used for spectroscopic analysis. The processing module 134 can extract spectroscopic information from this intensity signal in any of a variety of ways. For example, the processing module 134 can include a spectrum analyzer to perform infrared spectroscopy.

Figure 1B:
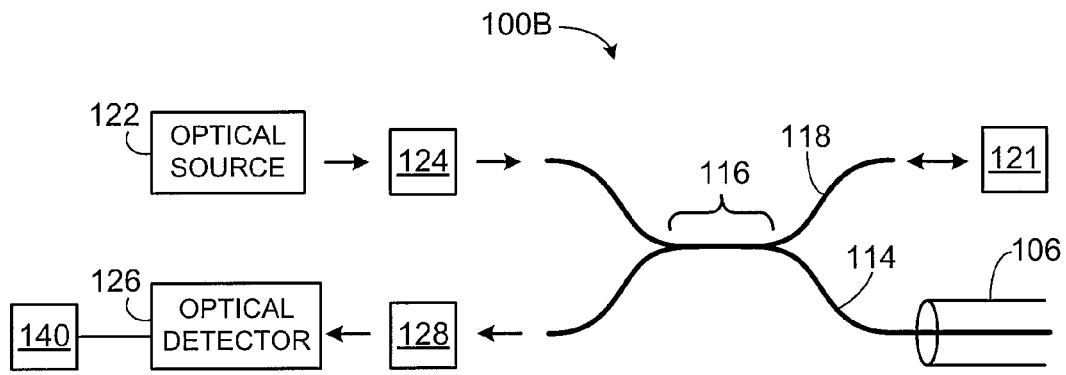

Referring to FIG. 1B, in a second embodiment, a VPDS 100B includes the second and the third optical waveguides (114 and 118) of the VPDS 100A, but not the first optical waveguide 108. The VPDS 100B uses the optical radiation coupled from the second and third optical waveguides for both sub-surface imaging and spectroscopic analysis.

Both the first embodiment of the VPDS 100A and the second embodiment of the VPDS 100B use a Michelson Interferometer (MI) topology. In the MI topology, a beamsplitter 116 splits the incoming light into a "measurement arm" and a "reference arm." Light in the measurement arm is transformed (e.g., in amplitude and/or phase) by scattering from a measurement object (the arterial wall 104 in this example). Light in the reference arm undergoes a group delay (in some cases a variable delay due to a path length change). Light from both arms recombines in the beamsplitter 116 to produce an interference signal.

In the second embodiment, a reflector 121 can be a variable-delay reflector that provides a variable group delay for the light in the third optical waveguide 118. This delayed light is combined with light returning through the second optical waveguide 114. In this case, a processing module 140 uses the envelope of the signal detected by the first optical detector 126 to extract information about the location of structural elements in the arterial wall 104 (i.e., sub-surface imaging). As the group delay of the reference arm is scanned, the interference signal yields information from different depths of the measurement object according to a coherence envelope of a limited-coherence light source (e.g., a broadband light source). Adittionally, the processing module 140 takes the Fourier-transform (FT) of the signal centered at a particular group delay to obtain the cumulative absorbance over a particular thickness of the arterial wall 104 (i.e., spectroscopic information).

Alternatively, in the second embodiment, the reflector 121 can be a stationary reflector and the processing module 140 can obtain sub-surface imaging information and spectroscopic information based on combined properties of, for example, the optical source 122, the optical coupler 128, and the optical detector 126. For example, the source 122 can emit narrowband radiation scanned over a range of wavelengths such that the optical coupler 128 and optical detector 126 generate a spectrally-resolved signal as a function of the scanned wavelength. Alternatively, the source 122 can emit broadband radiation including a range of wavelengths such that the optical coupler 128 and a "spectrally-sensitive" optical detector 126 generate a spectrally-resolved signal as a function of the detected wavelength. This spectrally-resolved signal contains the spectroscopic information in the form of the cumulative absorbance of the sample illuminated by the probe 106.

The cumulative absorbance of the sample can also be measured without a reflector 121 in the system. To do so, one performs optical frequency domain reflectometry to obtain the sub-surface imaging information from the spectrally-resolved signal. For example, the Fourier transform of the spectrally-resolved signal contains information about the location of structural elements in the sample illuminated by the probe 106.

Measurement of a known sample with the VPDS 100B is useful as a baseline measurement (e.g., to calibrate the system). In some cases, the baseline sample is one with no spectral features in the range of interest. Alternatively, a sample with well-characterized spectral features in the range of interest can be used.

Figure 1C:
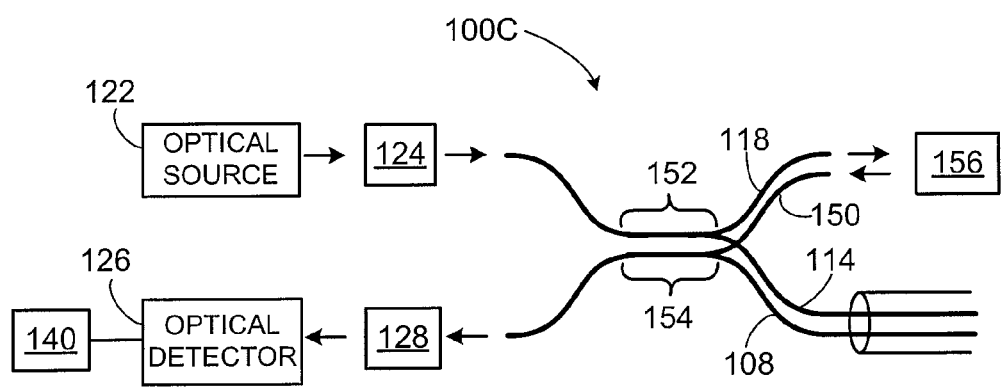

Referring to FIG. 1C, in a third embodiment, a VPDS 100C uses a Mach-Zender Interferometer (MZI) topology for sub-surface imaging. The VPDS 100C includes a first optical waveguide 108 and a second optical waveguide 114 each extending into the probe 106, and a third optical waveguide 118 coupled to a portion of the second optical waveguide 114 via a first beamsplitter 152. The VPDS 100C also includes a fourth optical waveguide 150 coupled to a portion of the first optical waveguide 108 via a second beamsplitter 154. Each of the first and second beamsplitters is a 50/50 fused-fiber 1×2 coupler with a 50% power splitting ratio, one input port and two output ports, or equivalently, two input ports and one output port.

In the MZI topology, the first beamsplitter 152 splits the incoming light from the optical source 122 into two paths. Light in a "measurement path" propagates in the second optical waveguide 114 and is transformed (e.g., in amplitude and/or phase) by scattering from a measurement object (the arterial wall 104 in this example). The scattered light is collected into the first optical waveguide 108 via the optical delivery and collection head 115 (FIG. 1A). Light in a "reference path" propagates in the third optical waveguide 118 toward a variable-delay coupler 156 that imparts a variable group delay to the light before coupling the light back into the fourth optical waveguide 150.

Light from the measurement path in the first optical waveguide 108 and the light from the reference path in the fourth optical waveguide 150 recombine in the second beamsplitter 154 to produce an interference signal at an optical detector 126. As in the MI topology, as the group delay of the reference path is scanned, the interference signal yields information from different depths of the measurement object according to a coherence envelope of a limited-coherence light source. As in VPDS 100B, the processing module 140 can obtain sub-surface imaging information and spectroscopic information based on combined properties of, for example, the optical source 122, the optical coupler 128, and the optical detector 126

Figure 1D:
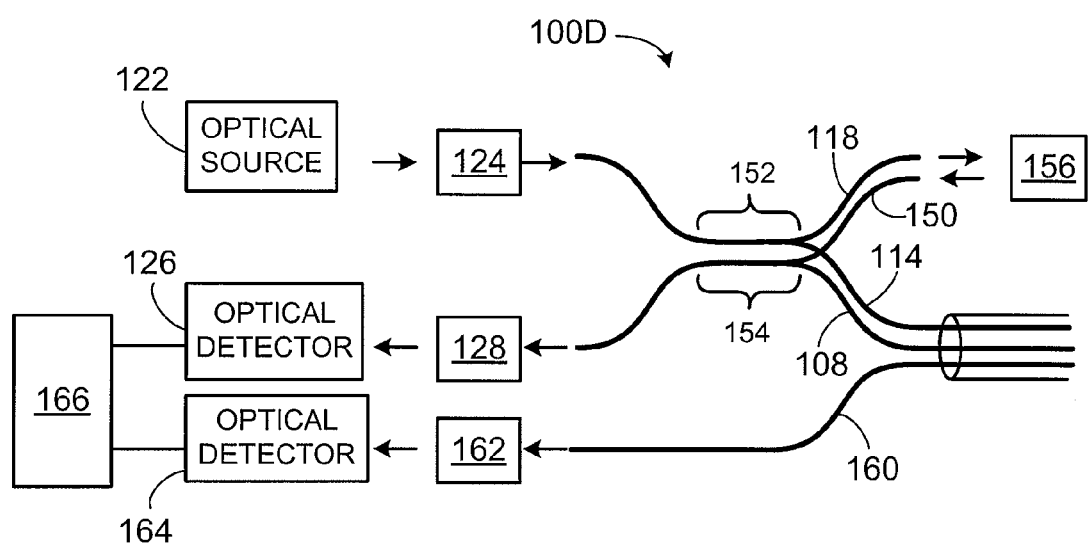

Referring to FIG. 1D, in a fourth embodiment, a VPDS 100D includes a fifth optical waveguide 160, an optical coupler 162, and an optical detector 164 for spectroscopic analysis, as in the VPDS 100A of the first embodiment, and uses a MZI topology for sub-surface imaging, as in the VPDS 100C of the third embodiment. Other embodiments including combinations or variations of these four embodiments are possible.

Referring again to FIG. 1A, during operation, the probe 106 is inserted along a blood vessel, typically an artery, using a guidewire (not shown). One using the VPDS 100A engages a motor 170 coupled to the probe 106. The motor 170 rotates the probe 106 at a rate between approximately 1 revolution per second and 400 revolutions per second. This causes the optical delivery and collection head 115 to trace a path around the inner circumference of the arterial wall 104. In one practice the probe 106 is inserted in discrete steps, with a complete rotation occurring at each such step. In this case, the spectroscopic and sub-surface imaging data can be collected along discrete circular paths. Alternatively, the probe 106 is inserted continuously, with axial translation and rotation occurring simultaneously. In this case, the spectroscopic and sub-surface imaging data are collected along continuous helical paths.

As it rotates, the optical delivery and collection head 115 redirects light placed on one of the optical waveguides by the optical source 122 to a scanning area 172. At the same time, the optical delivery and collection head 115 collects light re-emerging from the scanning area 172 and directs it into each optical waveguide in the probe that is configured to receive light for spectroscopic analysis and sub-surface imaging, as described above. The variable-delay reflector 120 or variable-delay coupler 156 is configured to scan the variable optical group delay by an amount corresponding to a coherence length of the optical source 122.

The collected spectroscopic data can be used to generate a three-dimensional spectral map of the arterial wall 104, and the collected sub-surface imaging data can be used to generate a three-dimensional morphological map of the arterial wall 104. Since the spectroscopic and sub-surface imaging data collected at a given time correspond to the same or similar region of the artery, the spectral map and the morphological map can be easily co-registered to match specific spectral and morphological features. As the probe 106 traverses an artery, both the spectroscopic data and the sub-surface imaging data can be used in real-time to diagnose vulnerable plaques, or identify other lesion types that have properties that can be identified by these two detection modalities. The probe 106 can optionally include structures for carrying out other diagnostic or treatment modalities in addition to the infrared spectroscopy and sub-surface imaging diagnostic modalities.

The optical delivery and collection head 115 (FIG. 1A) includes one or more light couplers in optical communication with distal ends of one or more optical waveguides at the distal end 110 of the probe 106. For example, in embodiments in which optical radiation for sub-surface imaging is delivered from and collected back into the same optical waveguide (e.g., VPDS 100A and VPDS 100B), the probe 106 can include only one optical waveguide for delivery and collection with the same optical waveguide used to collect the optical radiation for spectroscopic analysis and sub-surface imaging. Such embodiments can alternatively include more than one optical waveguide for separate collection of optical radiation for spectroscopic analysis and sub-surface imaging. In embodiments in which optical radiation for sub-surface imaging is delivered from one optical waveguide and collected into another optical waveguide (e.g., VPDS 100C and VPDS 100D), the probe 106 includes at least two optical waveguides.

The optical delivery and collection head 115 can use any of a variety of techniques to transmit optical radiation between the optical waveguides and the arterial wall. In some embodiments, the optical delivery and collection head 115 includes an atraumatic light-coupler configured to atraumatically contact the arterial wall. Such an atraumatic light-coupler can couple light directly without having to transmit the light through intervening media such as blood, as described below.

Figure 2:
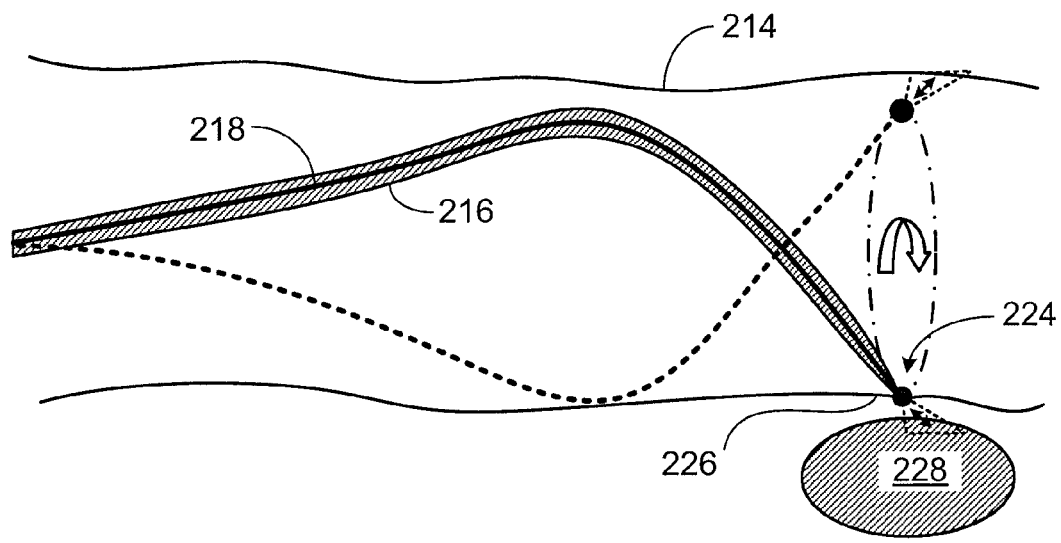
FIG. 2 is a schematic view of a probe in contact with the arterial wall.
Figure 3:
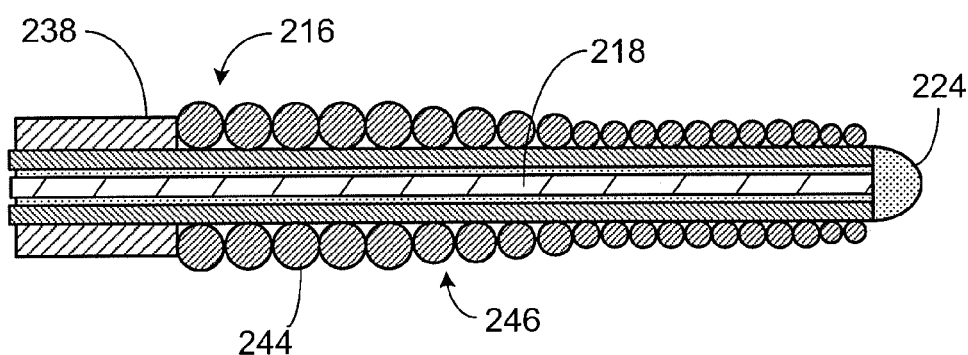
FIG. 3 is a cross-section of the probe of FIG. 2.

In a first embodiment, shown in FIGS. 2-3, an atraumatic light-coupler 224 at the distal end of the probe 216 rests on a contact area 226 on the arterial wall 214. When disposed as shown in FIG. 2, the atraumatic light-coupler 224 directs light traveling axially on the fiber 218 to the contact area 226. After leaving the atraumatic light-coupler 224, this light crosses the arterial wall 214 and illuminates structures 228 behind the wall 214. These structures 228 scatter some of the light back to the contact area 226, where it re-emerges through the arterial wall 214. The atraumatic light-coupler 224 collects this re-emergent light and directs it into the fiber 218.

Along a proximal section of the probe 216, as shown in FIG. 3, a rigid tube 238 encasing the fiber 218, enables the probe 216 to be pushed through the artery. Along a central and distal section of the probe 216, a coil wire 244 wound into a flexible coil-wire jacket 246 encases the fiber 218.

The coil wire 244 has a constant diameter along the central section. Along the distal section of the probe 216, the diameter of the coil wire 244 becomes progressively smaller. As a result, the distal section of the probe 216 is more flexible than its central section. This enhanced flexibility enables the distal section to follow the contour of the wall 214 without exerting unnecessary force against it.

Figure 4A:
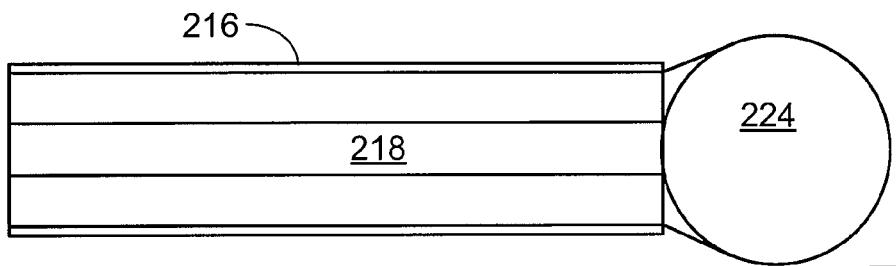
Figure 4B:
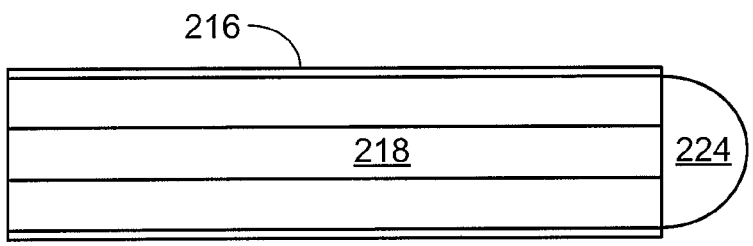
Figure 4C:
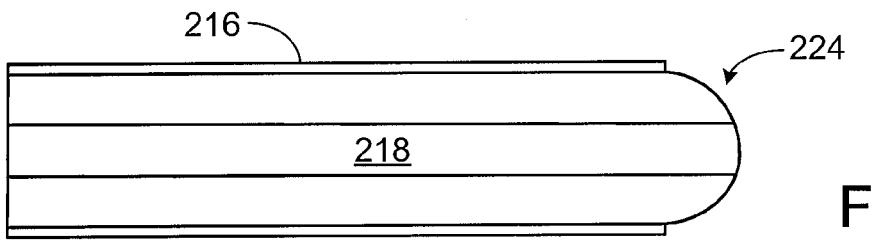
Figure 4D:
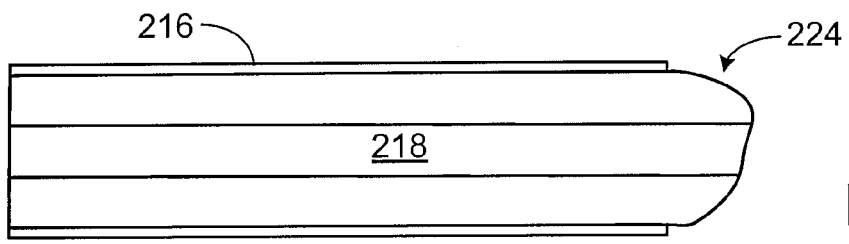
Figure 4E:
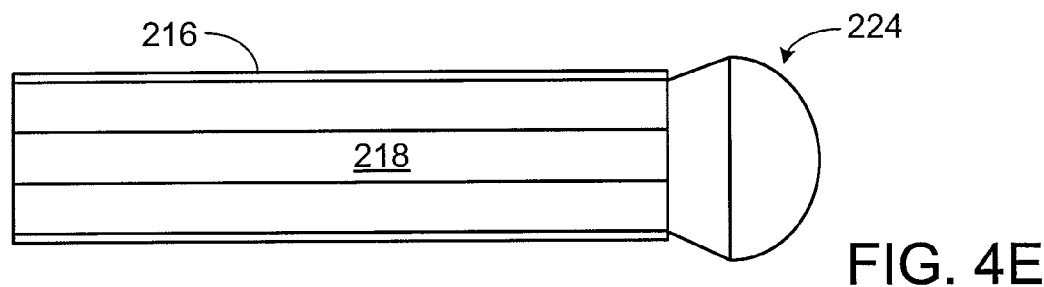

The atraumatic light-coupler 224 can be formed by attaching a lens assembly to a distal tip of the fiber 218, as shown in FIGS. 4A, 4B, and 4E, or by attaching a rounded glass tip to an angled fiber, as shown in FIGS. 4F-G. Alternatively, the atraumatic light-coupler 224 can be made integral with the fiber 218 by smoothing any sharp edges at its distal tip, as shown in FIGS. 4C-D.

In either case, the atraumatic light-coupler 224 can include a spherical lens, as shown in FIG. 4A, or a hemispherical lens, as shown in FIG. 4B. The atraumatic light-coupler 224 can also include more than one lens element, as shown in FIG. 4E.

Alternatively, the atraumatic light-coupler 224 can be integral with the fiber 218. For example, the distal tip of the fiber 218 can be formed into a plane having rounded edges and oriented at an angle relative to the plane of the fiber cross-section, as shown in FIG. 4D, or into a hemisphere, as shown in FIG. 4C.

In a second embodiment, shown in FIGS. 5A-C, a probe housing 259 extends through a cannula 260 parallel to, but radially displaced from a longitudinal axis thereof. A probe 216 is kept inside the probe housing 259 until it is ready to be deployed. Extending along the longitudinal axis of the cannula 260 is a guide-wire housing 261 forming a guide-wire lumen through which a guide-wire 263 extends.

The probe 216 includes one or more optical waveguides as in the vulnerable plaque detection systems 100A-100D described above. For embodiments in which the same optical waveguide is used to collect the light for spectroscopic analysis and sub-surface imaging (e.g., VPDS 100B and VPDS 100C), an optical fiber made of glass or plastic can be used to collect the scattered light. For embodiments in which a separate optical waveguide is used to collect light for spectroscopic analysis (e.g., VPDS 100A and VPDS 100D), the optical waveguide for spectroscopic analysis can include an optical fiber made of glass or plastic, or a bundle of such fibers. In one embodiment, the probe includes a bundle of 25 optical fibers, each 0.005 millimeters in diameter. The fiber(s) can be exposed, coated with a protective biocompatible layer and/or a lubricious layer such as polytetrafluoroethylene ("PTFE"), or encased in a coil-wire jacket. The optional coating or jacket around the fiber(s) could be round, and hence bendable in all directions, or flat, so as to suppress bending in undesired directions.

For embodiments in which a separate optical waveguide is used to collect light for spectroscopic analysis (e.g., VPDS 100A and VPDS 100D), the optical waveguide for spectroscopic analysis can alternatively include an annular waveguide of a double-clad fiber. A waveguide of this type and a corresponding optical delivery and collection head 115 are described filly in U.S. application Ser. No. 10/218,939 (Publication No. 2004/0034290), the contents of which are herein incorporated by reference.

The distal tip of the optical fiber 218 is capped by any of the atraumatic light-couplers 224 discussed above. When the distal end of the cannula 260 is just proximal to contact area 226, the probe 216 is pushed distally so that its distal tip extends past the distal end of the cannula 260. Alternatively, the probe 216 remains stationary while the cannula 260 is retracted, thereby exposing the probe 216.

The probe 216 is pre-formed so that a natural bend urges it outward, away from the axis of the cannula 260. As a result, when the probe 216 is extended out its housing 259 and beyond the distal end of the cannula 260, this natural bend places the atraumatic light-coupler 224 of the fiber 218 in contact with the arterial wall 214 distal to the cannula 260. The probe 216 is then rotated so that the atraumatic light-coupler 224 traces out a circular contact path along an inner circumference of the wall 214, as shown in FIGS. 5A and 5C.

A variety of ways are known for pre-forming a probe 216. For example, the probe 216 can be heated while in the desired shape. Or a coating over the fiber within the probe 216 can be applied and cured while the fiber is in the desired shape.

In a third embodiment, shown in FIGS. 5D-F, the cannula 260 has a proximal section 288 and a distal section 290 separated from each other by a circumferential gap 292. A guide wall 294 forms a truncated cone extending distally from a truncated end joined to the guide-wire housing 259 to a base joined to the distal section 290 of the cannula 260. The guide wall 294 thus serves to maintain the position of the proximal and distal sections 288, 290 of the cannula 260 relative to each other while preserving the circumferential gap 292 all the way around the cannula 260.

In use, the probe 216 is extended distally toward the guide wall 294, which then guides the probe 216 out of the circumferential gap 262. As was the case with the second embodiment (FIGS. 5A-C), the natural bend of the probe 216 urges the atraumatic tip 224 into contact with the arterial wall 214. Once the probe's atraumatic tip 224 contacts the wall 214, the probe 216 is rotated as shown in FIGS. 5D-F so that the atraumatic tip 224 sweeps a circumferential contact path on the arterial wall 214.

Figure 6A:
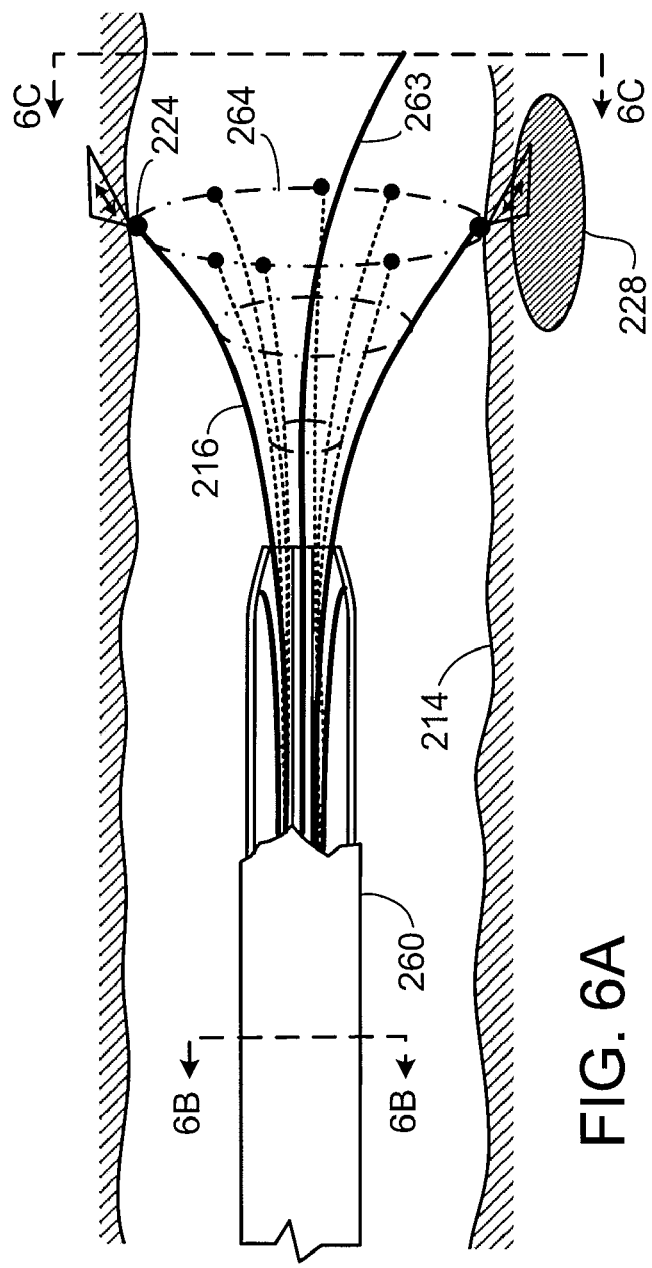
FIGS. 6A-F are schematic views of multi-probe spectroscopes.
Figure 6C:
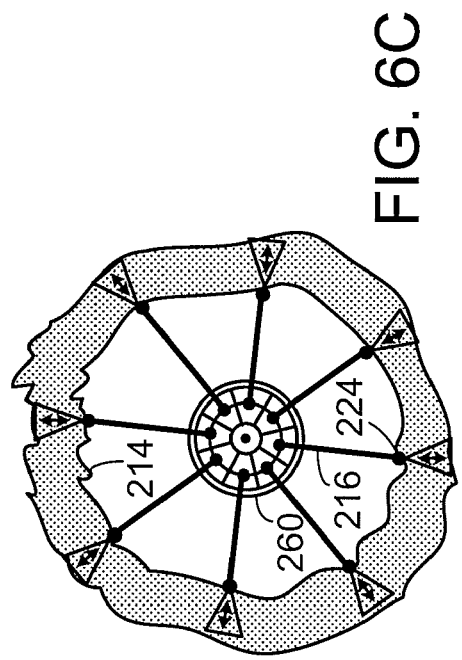
Figure 6B:
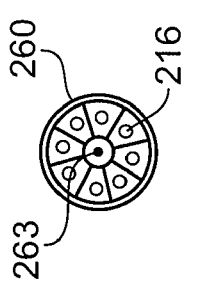

In a fourth embodiment, shown in FIGS. 6A-C, several probes 216 of the type discussed above in connection with FIGS. 5A-F pass through the cannula 260 at the same time. Optional spacer rings 264 are attached to the probes 262 at one or more points along their distal sections. The spacer rings 264 can be silicon webbing, plastic, Nitinol, or any other biocompatible material.

When deployed, the spacer rings 264 are oriented so as to lie in a plane perpendicular to the longitudinal axis of the cannula 260. The spacer rings 264 thus maintain the relative positions of the probes 216 during scanning of the wall 214. A multi-probe embodiment as shown in FIGS. 6A-C enables most of the circumference of an arterial wall 214 to be examined without having to rotate the probes 216.

In a fifth embodiment, shown in FIGS. 6D-F, the cannula 260 is as described in connection with the third embodiment (FIGS. 5D-F). The difference between this fifth embodiment and the third embodiment (FIGS. 5D-F) is that in the third embodiment, a single probe 216 extends through the circumferential gap 292, whereas in this fifth embodiment, several probes 216 circumferentially offset from one another extend through the circumferential gap 292. As a result, in the third embodiment, it is necessary to rotate the probe 216 to inspect the entire circumference of the arterial wall 214, whereas in the fifth embodiment, one can inspect most of the arterial wall 214 circumference without having to rotate the probes 216 at all.

Figure 7A:
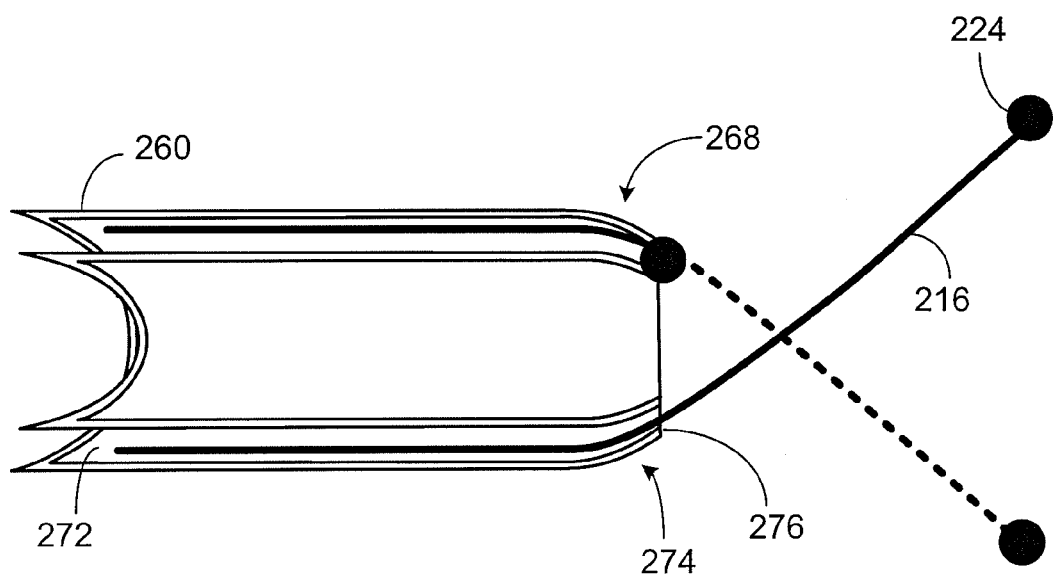
FIG. 7A is a schematic view of a probe emerging from a cannula having a tapered distal end.
Figure 7B:
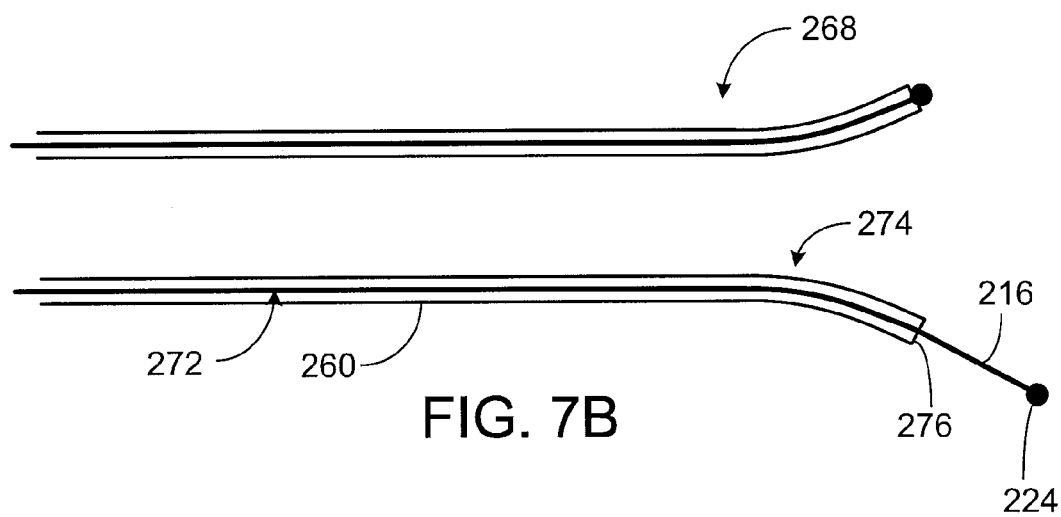
FIG. 7B is a schematic view of a probe emerging from a cannula having a flared distal end.

In a sixth embodiment, a cannula 260 has a tapered distal end 268, as shown in FIG. 7A, or a flared distal end 270, as shown in FIG. 7B. A channel 272 formed in the inner wall of the cannula 260 has a bend 274 proximal to an opening 276 at the distal end. This opening 276 defines a surface whose normal vector has both a radial component and an longitudinal component.

One operating the embodiments of FIGS. 7A and 7B pushes the probe 216 through the channel 272, which then guides it toward the opening 272. As the probe 216 exits the channel 272, it proceeds in the direction of the normal vector until its atraumatic light-coupler 224 contacts the arterial wall 214. In this case, the probe 216 need not be pre-formed to have a preferred shape since the channel 272 guides the probe 216 in the correct direction for reaching the wall 214.

In a seventh embodiment, shown in FIGS. 8A-B, a plurality of probes 216 passes through a cannula 260. The distal ends of the probes 216 are attached to anchor points circumferentially distributed around a hub 278. The hub 278 is coupled to a control wire 280 that enables it to be moved along the longitudinal axis of the cannula 260 to either deploy the probes 216 (FIG. 8A) or to retract the probes 216 (FIG. 8B). However, in other embodiments, the hub 278 remains stationary and it is the cannula 260 that is moved proximally and distally to either deploy or recover the probes 216.

The probes 216 are pre-formed to bow outward as shown in FIG. 8A so as to contact the arterial wall 214 at an intermediate point between the hub 278 and the cannula 260. Optional spacer rings 264, like those discussed in connection with FIGS. 6A-C, are attached to the probes 216 at one or more points along their distal sections to maintain their relative positions. In this seventh embodiment, the atraumatic light-coupler 224 includes a side-window 282 located at the intermediate point. The side window 282 faces radially outward so that when the probe 216 is fully deployed, the side window 282 atraumatically contacts the arterial wall 214.

An atraumatic light-coupler 224 for placement along the side of the probe 216 includes a right-angle reflector 284, such as a prism or mirror, placed in optical communication between the fiber 218 and the side window 282, as shown in FIG. 9B. Alternatively, an air gap 286 is placed in optical communication between the tip of an angle polished fiber 218 and the side-window 282, as shown in FIG. 9A.

FIGS. 9C-9D shows additional examples of atraumatic light-couplers 224 for placement along the side of the probe 216. In these examples, the side window 282 is formed by a portion of the fiber's cladding that is thin enough to allow passage of light. The side window 282 can be left exposed, as shown in FIG. 9C, or a diffraction grating 285 can be placed in optical communication with the side window 282 to further control the direction of the beam, as shown in FIG. 9D.

When the hub 278 and the cannula 260 are drawn together, as shown in FIG. 8B, they can easily be guided to a location of interest. Once the hub 278 and cannula 260 reach a location of interest, one either advances the hub 278 or retracts the cannula 260. In either case, the probes 216 are released from the confines of the cannula 260, as shown in FIG. 8A. Once free of the radially restraining force applied by the cannula's inner wall, the probes 216 assume their natural shape, bowing outward, as shown in FIG. 8B, so that their respective side-windows 282 atraumatically contact the arterial wall 214. The atraumatic light-couplers 224 guide light from the light source 250 through the side windows 282. At the same time, the atraumatic light-couplers 224 recover re-emergent light from the wall 214 through the side windows 282 and pass it into the fibers 218, which guide that light to an optical detector.

When the examination of the wall 214 is complete, the hub 278 and cannula 260 are brought back together, as shown in FIG. 8B, and the probes 216 are once again confined inside the cannula 260.

Figure 6D:
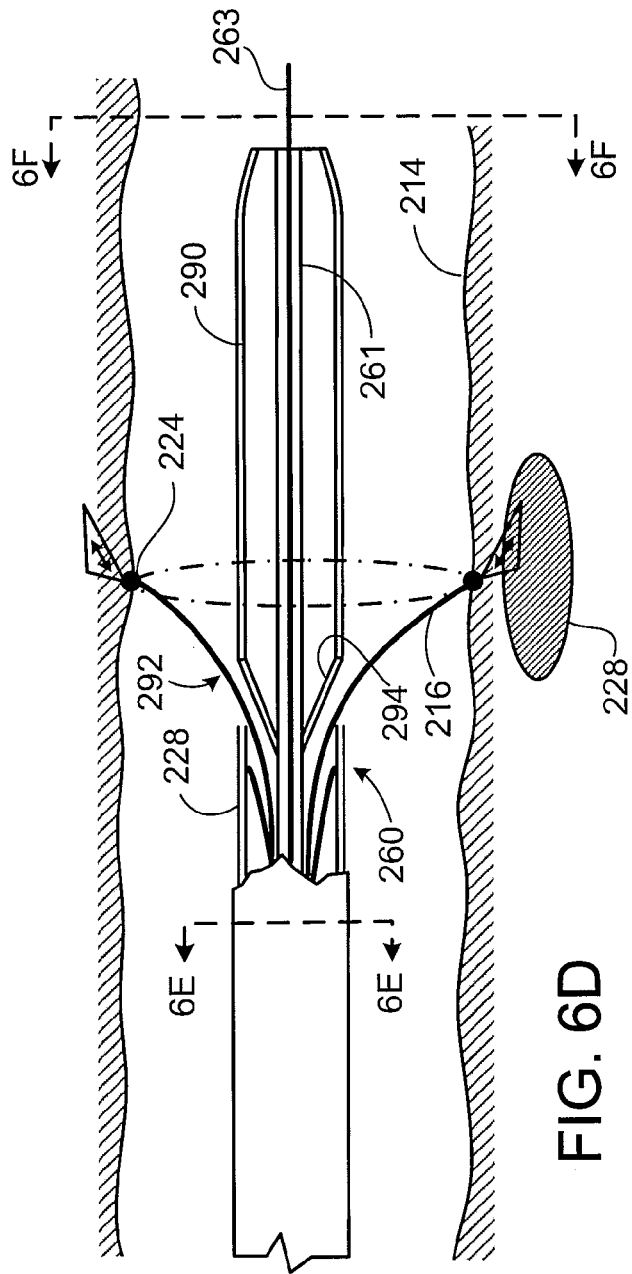
Figure 6F:
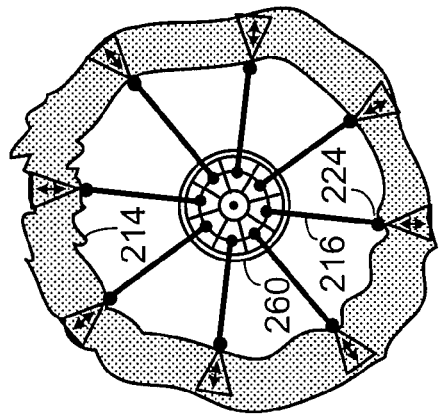
Figure 6E:
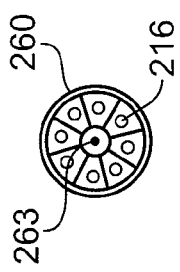

In an eighth embodiment, shown in FIGS. 8C-D, the cannula 260 has a proximal section 288 and a distal section 290 separated by a circumferential gap 292, as described in connection with the third embodiment (FIGS. 5D-F) and the fifth embodiment (FIGS. 6D-F). Unlike the third and fifth embodiments, in which the distal tips of the probes 216 atraumatically contact the wall 214, in the eighth embodiment the distal tips of the probes 216 are attached to a hub 278 at the distal section 290 of the cannula 260. Like the probes 216 of the seventh embodiment, the probes 216 of the eighth embodiment have side windows 82 at intermediate points for atraumatically contacting the arterial wall 214. An actuator (not shown) is mechanically coupled to selectively apply tension to the probes 216. When the probes 216 are under tension, they lie against the distal section 290 of the cannula 260, as shown in FIG. 8D. When probes 216 are relaxed, they spring radially outward, away from the distal section 290, enough so that the side windows 282 at the intermediate sections atraumatically contact the arterial wall 214.

In use, the cannula 260 is guided to a region of interest with the probes 216 placed under tension. The probes 216 are thus drawn against the cannula 260, as shown in FIG. 8B. Once at the region of interest, the tension is released, and the probes 216 spring radially outward, as shown in FIG. 8A, so that the side windows 282 atraumatically contact the wall 214. After data collection, the probes 216 are again placed under tension to draw them back against the cannula 260, as shown in FIG. 8B.

In the seventh and eighth embodiments, a particular probe 216 emerges from the cannula 260 at an exit point and re-attaches to the hub 278 at an anchor point. In a cylindrical coordinate system centered on the axis of the cannula 260, the exit point and the anchor point have different axial coordinates but the same angular coordinate. However, as FIGS. 8E and 8F illustrate, this need not be the case.

Figure 8E:
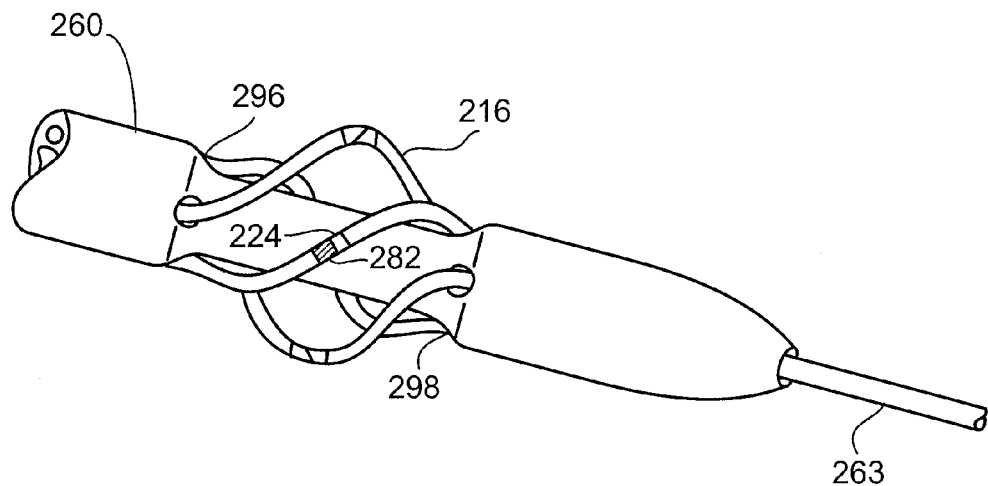

FIG. 8E shows a ninth embodiment in which a cannula 260 has a plurality of exit holes 296 and a corresponding plurality of entry holes 298. Each probe 216 exits the cannula 260 through an exit hole 296 and re-enters the cannula 260 through an entry hole 296 that is circumferentially offset from its corresponding exit hole. This results in the helical arrangement shown in FIG. 8E. The extent of the circumferential offset defines the pitch of the helix.

The distal ends of the probe 216 are attached to a hub 278 (not shown) inside the cannula 260. Each probe 216 has a side window 282 between the exit hole and the corresponding entry hole. A control wire 280 within the cannula 260 (not shown) deploys the probes 216, as shown, or retracts them so that they rest against the exterior of the cannula 260. A guide-wire 263 passing through the cannula 260 and exiting out the distal tip thereof enables the cannula 260 to be guided to a region of interest.

Figure 8F:
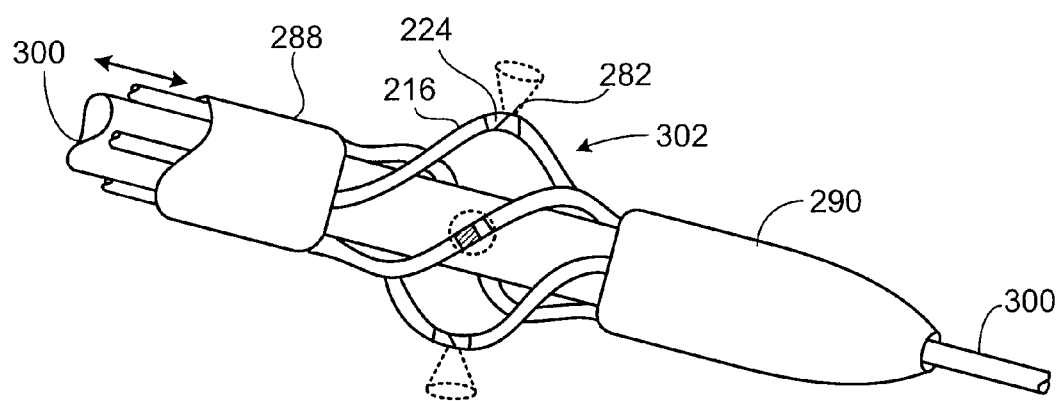

FIG. 8F shows a tenth embodiment in which a cannula 260 has a distal section 288 and a proximal section 290. The proximal and distal sections of the cannula 260 surround a central shaft 300 having an exposed portion 302. Probes 216 extend axially through a gap between the shaft and the cannula 260. The probes 216 are anchored at their distal ends at circumferentially displaced anchor points on a hub 278 attached to the shaft 300. The circumferential offset causes the helical configuration of the probes 216 in FIG. 8F. The extent of this circumferential offset defines a pitch of the helix.

An actuator (not shown) selectively applies tension to the probes 216. When the probes 216 are under tension, they retract against the exposed portion 302 of the central shaft 300. When the probes 216 are relaxed, they assume the configuration shown in FIG. 8F, in which they spring radially outward from the exposed portion 302 of the central shaft 300 so that their side windows 282 atraumatically contact the arterial wall 214.

In the embodiments described thus far, the probes 216 and the cannula 260 have been separate structures. However, the probes 216 can also be integrated, or otherwise embedded in the cannula 260. In this case, portions of the cannula 260 extend radially outward to contact the arterial wall 214.

Figure 8G:
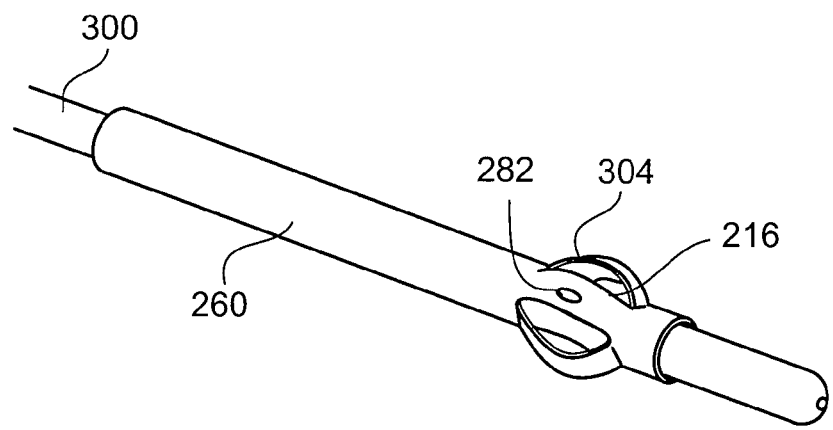
FIGS. 8G-K are schematic views of spectroscopes in which the probes are integrated into the cannula.
Figure 8H:
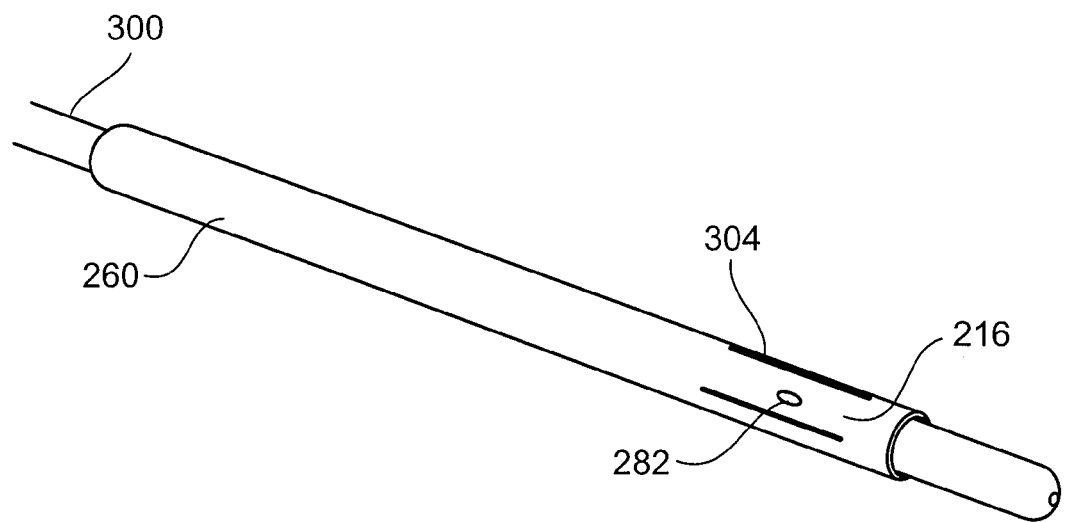

FIGS. 8G and 8H show an eleventh embodiment in a deployed and retracted state, respectively. The eleventh embodiment includes slots 304 cut into the wall of the cannula 260 enclosing an internal shaft 300. Pairs of adjacent slots 304 define probe portions 216 of the cannula 260. The probe portions 216 buckle outward when the distal tip of the cannula 260 is pulled proximally, as shown in FIG. 8G. When the distal tip of the cannula 260 is extended, the probe portions 216 lay flat against the shaft 300, as shown in FIG. 8H.

Each probe portion 216 has a side window 282 for atraumatically contacting the wall 214 when the probe portion 216 is deployed. The side window 282 is in optical communication with an atraumatic coupler 224. An optical fiber embedded within the wall of the cannula 260 provides an optical path to and from the atraumatic coupler 224.

Figure 8I:
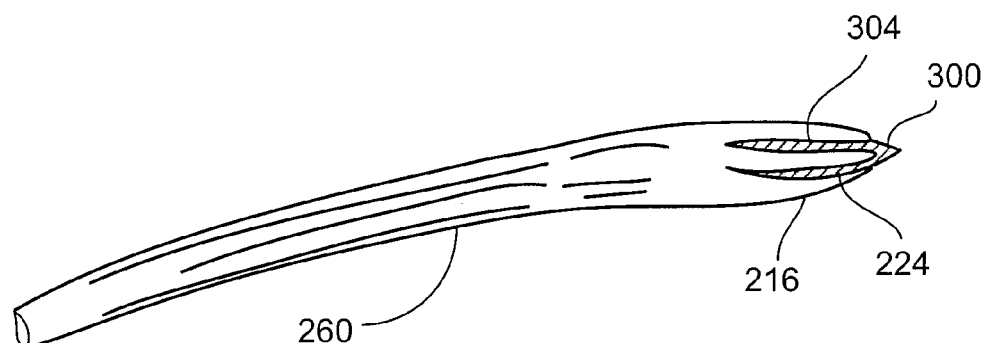
Figure 8J:
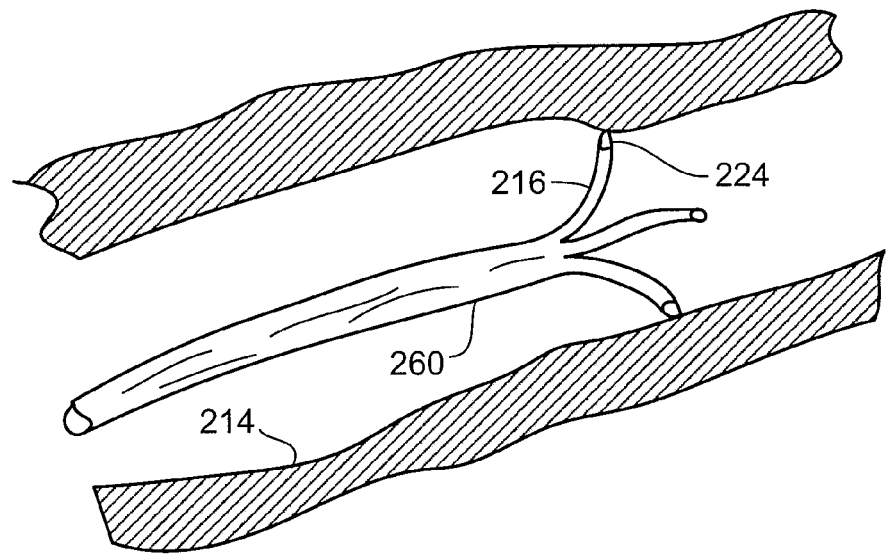

FIGS. 8I-J show a twelfth embodiment in a deployed and retracted state. The twelfth embodiment includes slots 304 cut into the wall of the cannula 260 enclosing an internal shaft 300. Unlike the slots 304 in the eleventh embodiment, the slots 304 in the twelfth embodiment extend all the way to the distal tip of the cannula. Pairs of adjacent slots 304 define probe portions 216 of the cannula 260.

Figure 8K:
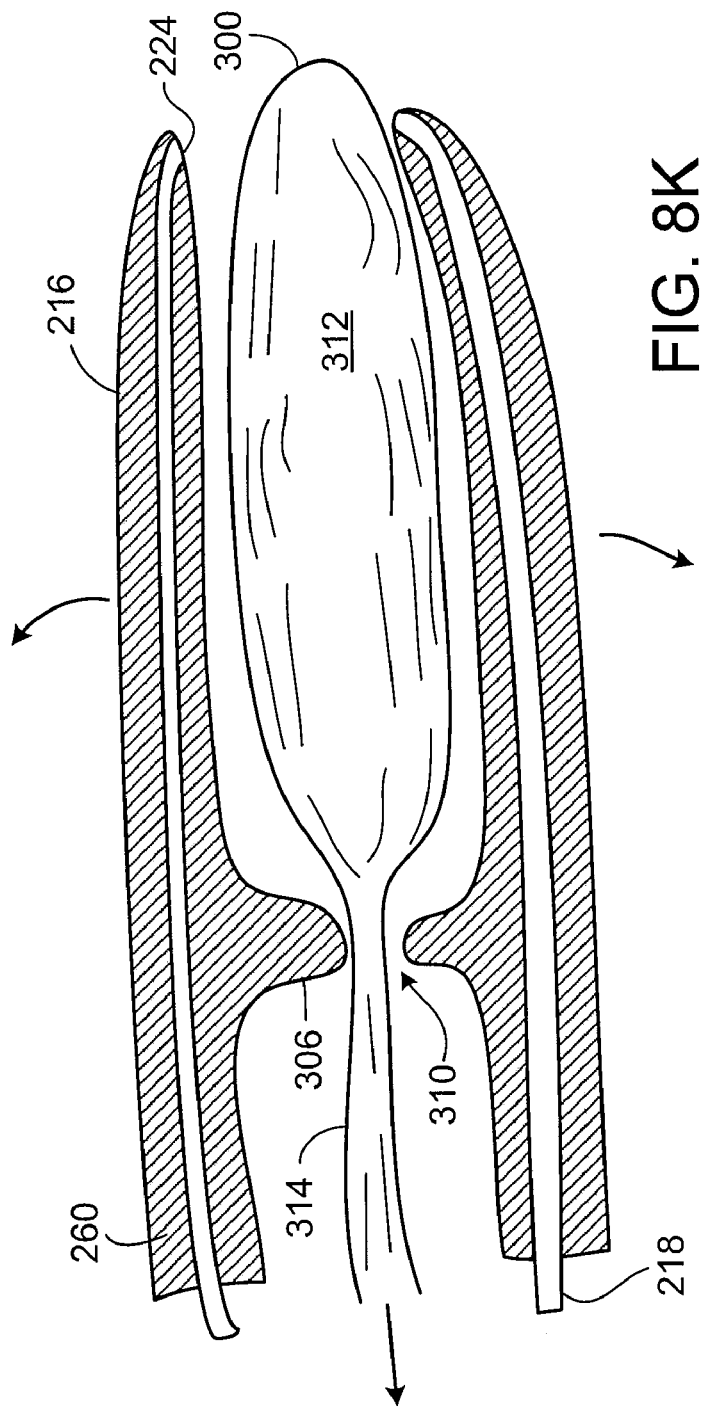

As shown in the cross-section of FIG. 8K, the cannula 260 includes radially-inward projections 306 forming a throat 310. The shaft 100 has a bulbous portion 312 distal to the throat 310 and a straight portion 314 extending proximally through the throat 310 to join the bulbous portion 312. The probe portions 216 are biased to rest against the bulbous portion 312 of the shaft 300, as shown in FIG. 8I. When the shaft 300 is drawn proximally, the bulbous portion 312 wedges against the projections 306. This forces the probe-portions 216 to pivot radially outward, as shown in FIG. 8J.

Each probe portion 216 has an atraumatic coupler 224 at its distal tip for atraumatically contacting the wall 214 when the probe portion 216 is deployed. An optical fiber embedded within the wall of the cannula 260 provides an optical path to and from the atraumatic coupler 224.

The optical delivery and collection head 115 can use other techniques to transmit optical radiation between the optical waveguides and the arterial wall. In some embodiments, the optical delivery and collection head 115 includes one or more beam redirectors.

Figure 10:
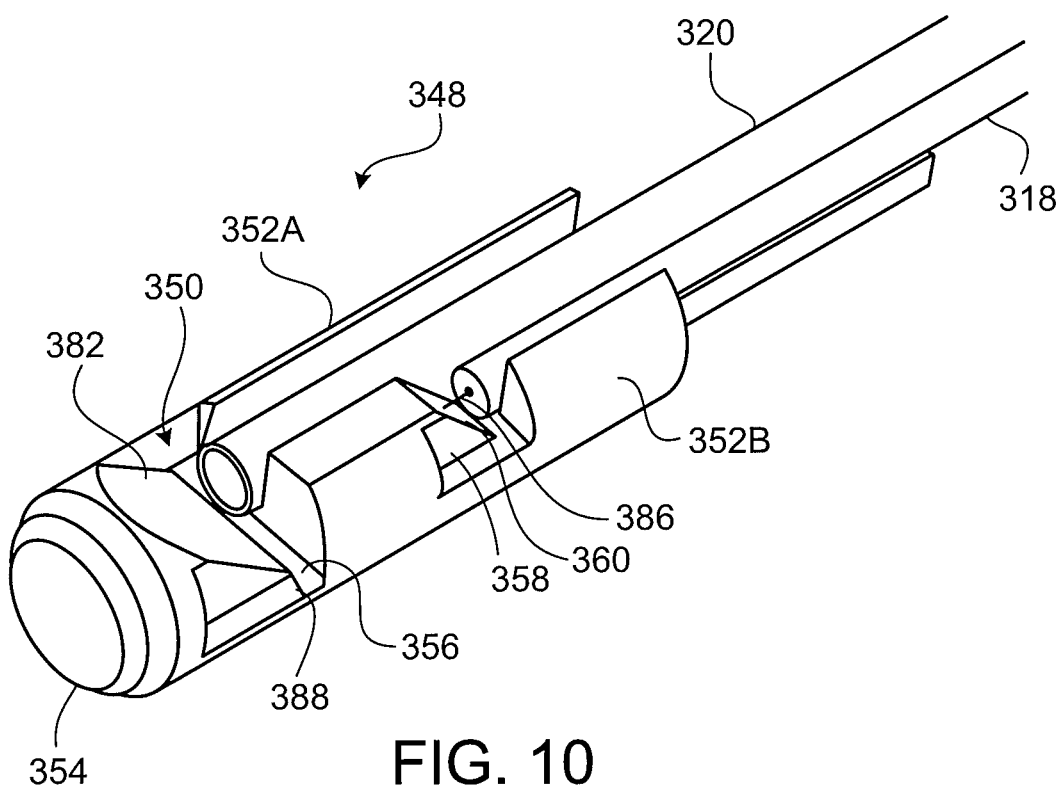
FIG. 10 is a view of an optical bench of an optical delivery and collection head.

FIG. 10 shows an optical bench 348 in which are seated the collection fiber 320 and the delivery fiber 318. The optical bench 348 is seated in a recess 350 between first and second side walls 352A-B of the distal end of a housing 354. The housing 354 is in turn coupled to the distal end of the torque cable 328. The recess 350 is just wide enough to enable the collection fiber 320 and the delivery fiber 318 to nestle adjacent to each other. A floor 356 extending between the first and second side walls 352A-B and across the recess 350 supports both the collection and delivery fibers 318, 320.

Just distal to the end of the delivery fiber 318, a portion of the optical bench 348 forms a frustum 358. The frustum 358 extends transversely only half-way across the optical bench 48, thereby enabling the collection fiber 320 to extend distally past the end of the delivery fiber 318.

The frustum 358 has an inclined surface facing the distal end of the delivery fiber 318 and a vertical surface facing the distal end of the optical bench 348. The inclined surface forms a 135 degree angle relative to the floor 356. However, other angles can be selected depending on the direction in which light from the delivery fiber 318 is to be directed. A reflective material coating the inclined surface forms a beam redirector, which in this case is a delivery mirror 360. When light exits axially from the delivery fiber 318, the delivery mirror 360 intercepts that light and redirects it radially outward to the arterial wall 214. Examples of other beam redirectors include prisms, lenses, diffraction gratings, and combinations thereof.

The collection fiber 320 extends past the end of the delivery fiber 318 until it terminates at a plane that is coplanar with the vertical face of the frustum 358. Just beyond the distal end of the collection fiber 320, a portion of the optical bench 348 forms an inclined surface extending transversely across the optical bench 348 and making an angle greater than 135 degrees relative to the floor 356. A reflective material coating the inclined surface forms a collection mirror 382.

A delivery-fiber stop 386 molded into the optical bench 348 proximal to the frustum 358 facilitates placement of the delivery fiber 318 at a desired location proximal to the delivery mirror 360. Similarly, a collection-fiber stop 388 molded into the optical bench 348 just proximal to the collection mirror 382 facilitates placement of the collection fiber 320 at a desired location proximal to the collection mirror 382.

Other types of beam redirecting techniques are possible including any combination of techniques described fully in U.S. Pat. No. 6,654,630 and U.S. Pat. No. 6,701,181, the contents of which are herein incorporated by reference.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. An apparatus for detecting vulnerable plaque within a lumen defined by an intraluminal wall, the apparatus comprising:
 a probe having a distal portion and a proximal portion;
 an optical waveguide extending along the probe, the optical waveguide being configured to carry optical radiation between the distal and proximal portions, and having a distal end in communication with the intraluminal wall;
 an interferometer coupled to the optical waveguide and configured to provide an interference signal for sub-surface imaging of the intraluminal wall;
 a processing module configured to provide spectroscopic information about the intraluminal wall from detected intensity of light collected from the intraluminal wall; and
 an optical source configured to couple optical radiation into the optical waveguide, wherein the optical source is configured to emit narrowband optical radiation scanned over a range of wavelengths to form the interference signal for sub-surface imaging and the spectroscopic information provided from the detected intensity of light collected from the intraluminal wall.

2. The apparatus of claim 1, wherein the processing module is configured to receive the detected intensity of light collected from the intraluminal wall by the optical waveguide.

3. The apparatus of claim 1, further comprising:
 a second optical waveguide extending along the probe, the second optical waveguide being configured to carry optical radiation between the distal and proximal portions, and having a distal end in communication with the intraluminal wall.

4. The apparatus of claim 3, wherein the processing module is configured to receive the detected intensity of light collected from the intraluminal wall by the second optical waveguide.

5. The apparatus of claim 1, wherein the interferometer is configured to provide an interference signal for sub-surface imaging by performing optical coherence tomography.

6. The apparatus of claim 1, wherein the interferometer is configured to provide an interference signal for sub-surface imaging by performing optical frequency domain reflectometry.

7. The apparatus of claim 1, wherein the processing module is configured to provide a cumulative absorbance over a particular thickness of the intraluminal wall from the detected intensity of light collected from the intraluminal wall.

8. The apparatus of claim 1, wherein the optical waveguide has a distal end in communication with the intraluminal wall through an atraumatic light-coupler configured to atraumatically contact the intraluminal wall.

9. An apparatus for detecting vulnerable plaque within a lumen defined by an intraluminal wall, the apparatus comprising:
 a probe having a distal portion and a proximal portion;
 a first optical waveguide extending along the probe, the first optical waveguide being configured to carry optical radiation between the distal and proximal portions, and having a distal end in communication with an area of the intraluminal wall;
 a second optical waveguide extending along the probe, the second optical waveguide being configured to carry optical radiation between the distal and proximal portions, and having a distal end in communication with the area of the intraluminal wall;
 a third optical waveguide coupled to a portion of the second optical waveguide;
 a fourth optical waveguide coupled to a portion of the first optical waveguide:
 an optical source configured to couple optical radiation into the second and third optical waveguides;
 a variable-delay coupler configured to couple optical radiation from the third optical waveguide into the fourth optical waveguide with a variable optical group delay, wherein the variable-delay coupler is configured to scan the variable optical group delay by an amount corresponding to a coherence length of a source of optical radiation, and an optical detector configured to receive optical radiation from the first and fourth optical waveguides.

10. The apparatus of claim 9, further comprising:

an optical coupler in optical communication with the distal end of the first optical waveguide, the optical coupler being configured to transmit optical radiation between the first optical waveguide and the intraluminal wall.

11. The apparatus of claim 10, wherein the optical coupler comprises an atraumatic light-coupler configured to atraumatically contact the intraluminal wall.

12. The apparatus of claim 9, further comprising:

an optical coupler in optical communication with the distal end of the second optical waveguide, the optical coupler being configured to transmit optical radiation between the second optical waveguide and the intraluminal wall.

13. The apparatus of claim 9, wherein the second optical waveguide is configured to provide light to the intraluminal wall, and the third optical waveguide is configured to provide reference light that is combined with light from the first optical waveguide collected from the intraluminal wall to provide an interference signal for sub-surface imaging of the intraluminal wall.

14. The apparatus of claim 9, further comprising:

an optical coupler in optical communication with the distal end of the first optical waveguide and the distal end of the second optical waveguide, the optical coupler being configured to transmit optical radiation from the second optical waveguide to the intraluminal wall and from the intraluminal wall to the first optical waveguide.

15. A method for detecting vulnerable plaque within a lumen defined by an intraluminal wall, the method comprising:

inserting a distal portion of a probe into the lumen;

providing optical radiation to the intraluminal wall through an optical waveguide extending along the probe;

combining reference optical radiation with optical radiation scattered from the intraluminal wall, and returning through the optical waveguide, to provide an interference signal for sub-surface imaging of the intraluminal wall;

processing a detected intensity of light collected from the intraluminal wall to extract spectroscopic information;

generating a morphological map of the intraluminal wall based on the interference signal;

generating a spectral map of the intraluminal wall based on the spectroscopic information; and co-registering portions of the morphological map and the spectral map collected at a given time corresponding to a given portion of the intraluminal wall.

16. An apparatus for detecting vulnerable plague within a lumen defined by an intraluminal wall, the apparatus comprising:

a probe having a distal portion and a proximal portion;

an optical waveguide extending along the probe, the optical waveguide being configured to carry optical radiation between the distal and proximal portions, and having a distal end in communication with the intraluminal wall through an atraumatic light-coupler configured to atraumatically contact the intraluminal wall;

an interferometer coupled to the optical waveguide and configured to provide an interference signal for sub-surface imaging of the intraluminal wall;

a processing module configured to provide spectroscopic information about the intraluminal wall from detected intensity of light collected from the intraluminal wall; and an optical source configured to couple optical radiation into the optical waveguide, wherein the optical source is configured to emit broadband optical radiation that includes a range of wavelengths to form the interference signal for sub-surface imaging and the spectroscopic information provided from the detected intensity of light collected from the intraluminal wall.

17. The apparatus of claim 1, wherein the optical waveguide has a distal end in communication with the intraluminal wall through an atraumatic light-coupler configured to atraumatically contact the intraluminal wall.

* * * * *

UNITED STATES PATENT AND TRADEMARK OFFICE
CERTIFICATE OF CORRECTION

| | | |
|---|---|---|
| PATENT NO. | : 7,450,241 B2 | Page 1 of 1 |
| APPLICATION NO. | : 11/241726 | |
| DATED | : November 11, 2008 | |
| INVENTOR(S) | : Andres F. Zuluaga | |

It is certified that error appears in the above-identified patent and that said Letters Patent is hereby corrected as shown below:

Column 14, line 61, in claim 9, delete "waveguide:" and insert -- waveguide; --, therefor.

Column 16, line 13, in claim 16, delete "plague" and insert -- plaque --, therefor.

Signed and Sealed this

Twentieth Day of January, 2009

JON W. DUDAS
*Director of the United States Patent and Trademark Office*